United States Patent
Lee et al.

(10) Patent No.: US 11,459,594 B2
(45) Date of Patent: Oct. 4, 2022

(54) FRUCTOSE-4-EPIMERASE AND METHOD OF PREPARING TAGATOSE USING THE SAME

(71) Applicant: CJ CHEILJEDANG CORPORATION, Seoul (KR)

(72) Inventors: Young Mi Lee, Seoul (KR); Eul Soo Park, Seoul (KR); Il Hyang Park, Seoul (KR); Sun Mi Shin, Seoul (KR); Sung Jae Yang, Seoul (KR); Ran Young Yoon, Seoul (KR); Eun Jung Choi, Seoul (KR); Seong Bo Kim, Seoul (KR); Seung Won Park, Seoul (KR)

(73) Assignee: CJ CHEILJEDANG CORPORATION, Seoul (KR)

(*) Notice: Subject to any disclaimer, the term of this patent is extended or adjusted under 35 U.S.C. 154(b) by 0 days.

(21) Appl. No.: 17/280,854

(22) PCT Filed: Sep. 27, 2019

(86) PCT No.: PCT/KR2019/012612
§ 371 (c)(1),
(2) Date: Mar. 26, 2021

(87) PCT Pub. No.: WO2020/067781
PCT Pub. Date: Apr. 2, 2020

(65) Prior Publication Data
US 2022/0025420 A1 Jan. 27, 2022

(30) Foreign Application Priority Data

Sep. 28, 2018 (KR) .................. 10-2018-0116609
Oct. 1, 2018 (KR) .................. 10-2018-0117237
Aug. 14, 2019 (KR) .................. 10-2019-0099826

(51) Int. Cl.
*C12N 9/88* (2006.01)
*C12N 15/52* (2006.01)
(Continued)

(52) U.S. Cl.
CPC ................ *C12P 19/24* (2013.01); *C12N 1/20* (2013.01); *C12N 9/88* (2013.01); *C12N 15/52* (2013.01); *C12N 15/70* (2013.01)

(58) Field of Classification Search
None
See application file for complete search history.

(56) References Cited

U.S. PATENT DOCUMENTS

2002/0159976 A1* 10/2002 Glenn .................. C07K 14/335
424/93.2
2018/0216146 A1 8/2018 Wichelecki
2022/0025420 A1* 1/2022 Lee .......................... C12N 9/88

FOREIGN PATENT DOCUMENTS

KR 10-0964091 B1 6/2010
KR 10-2015-0025703 A 3/2015
(Continued)

OTHER PUBLICATIONS

GenBank Accession No. HAN94648.1, published Sep. 5, 2018 (Year: 2018).*

(Continued)

*Primary Examiner* — Richard C Ekstrom
(74) *Attorney, Agent, or Firm* — Squire Patton Boggs (US) LLP

(57) ABSTRACT

Provided are a fructose-4-epimerase variant having tagatose conversion activity, and a method of producing tagatose using the same.

28 Claims, 4 Drawing Sheets
Specification includes a Sequence Listing.

(51) Int. Cl.
  *C12N 15/72* (2006.01)
  *C12N 1/20* (2006.01)
  *C12P 19/24* (2006.01)
  *C12N 15/70* (2006.01)

(56) References Cited

FOREIGN PATENT DOCUMENTS

| KR | 10-2016-0012001 A | 2/2016 |
| KR | 10-2017-0015250 A | 2/2017 |
| KR | 10-2018-0027962 A | 3/2018 |
| WO | WO 2015-016544 A1 | 2/2015 |
| WO | WO 2017-167255 A1 | 10/2017 |

OTHER PUBLICATIONS

UniProt Accession No. A0A1I7JMJ7_9FIRM, published Nov. 22, 2017 (Year: 2017).*
UniProt Accession No. A0A096B3W3_FLAPL, published Aug. 30, 2017 (Year: 2017).*
International search report and written opinion of PCT/KR2019/012612 dated Feb. 3, 2020 together with the English translation of the International search report (total of 9 pages).
Jain et al., "Arapid, efficient, and economical inverse polymerase chain reaction-based method forgenerating a site saturation mutant library", Analytical Biochemistry 449 (2014) pp. 90-98.
Knight et al. "Analyzing partially randomized nucleic acid pools: straight dope on doping", Nucleic Acids Research, 2003, vol. 31, No. 6 e30; DOI: 10.1093/nar/gng030.
Tang et al., Construction of "small-intelligent" focused mutagenesis libraries using well-designed combinatorial degenerate primers, BioTechniques 52:149-158 (Mar. 2012), doi 10.2144/000113820.
Brinkkötter et al., "Two class IID-tagatose-bisphosphate aldolases from enteric bacteria", Arch. Microbiol., 2002, vol. 177, pp. 410-419.
GenBank Accession No. WP_015868068, "D-tagatose-bisphosphate aldolase, class II, non-catalytic subunit [Kosmotoga olearia]", Oct. 8, 2019.
Lee et al., "Structure-based prediction and identification of 4-epimerization activity of phosphate sugars in class II aldolases", Scientific Reports, 7:1934 | DOI:10.1038/s41598-017-02211-3.

* cited by examiner

[FIG. 1]
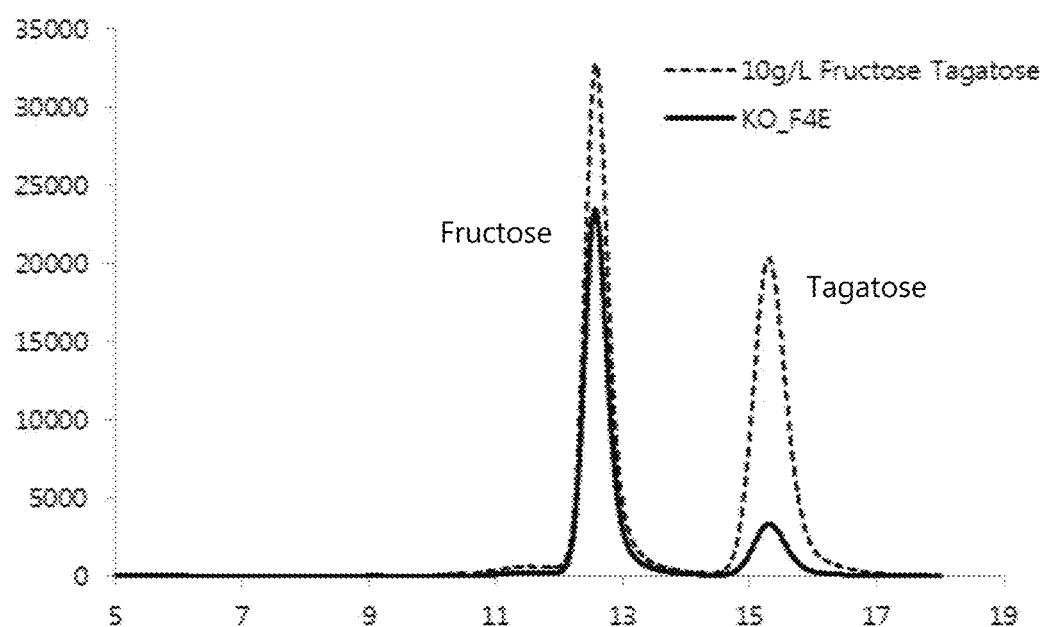

[FIG. 2]
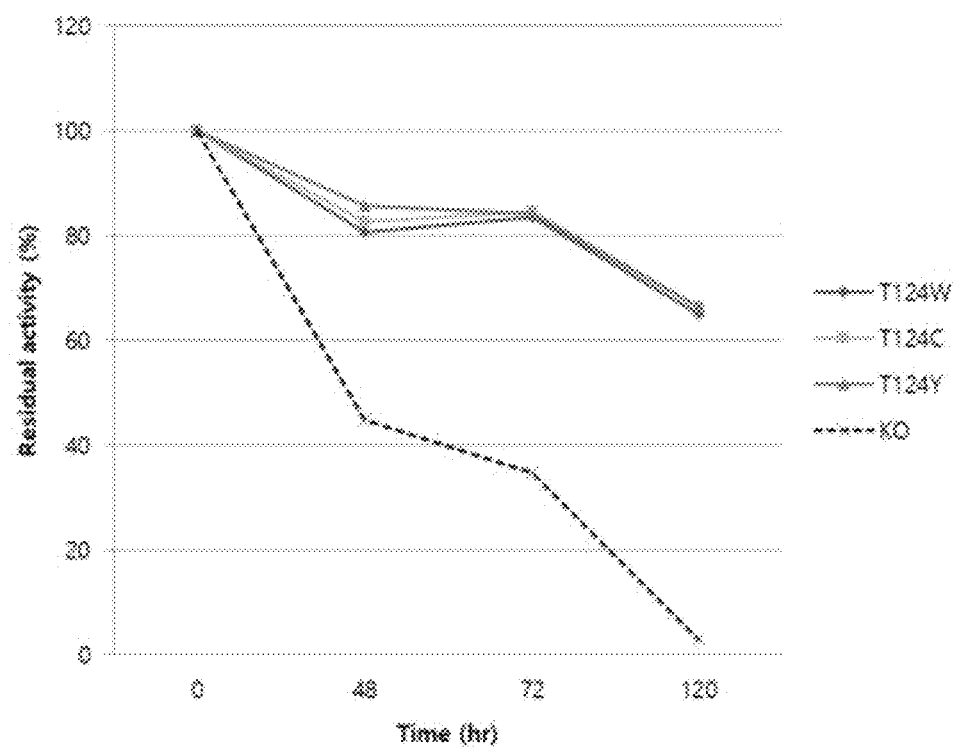

[FIG. 3]
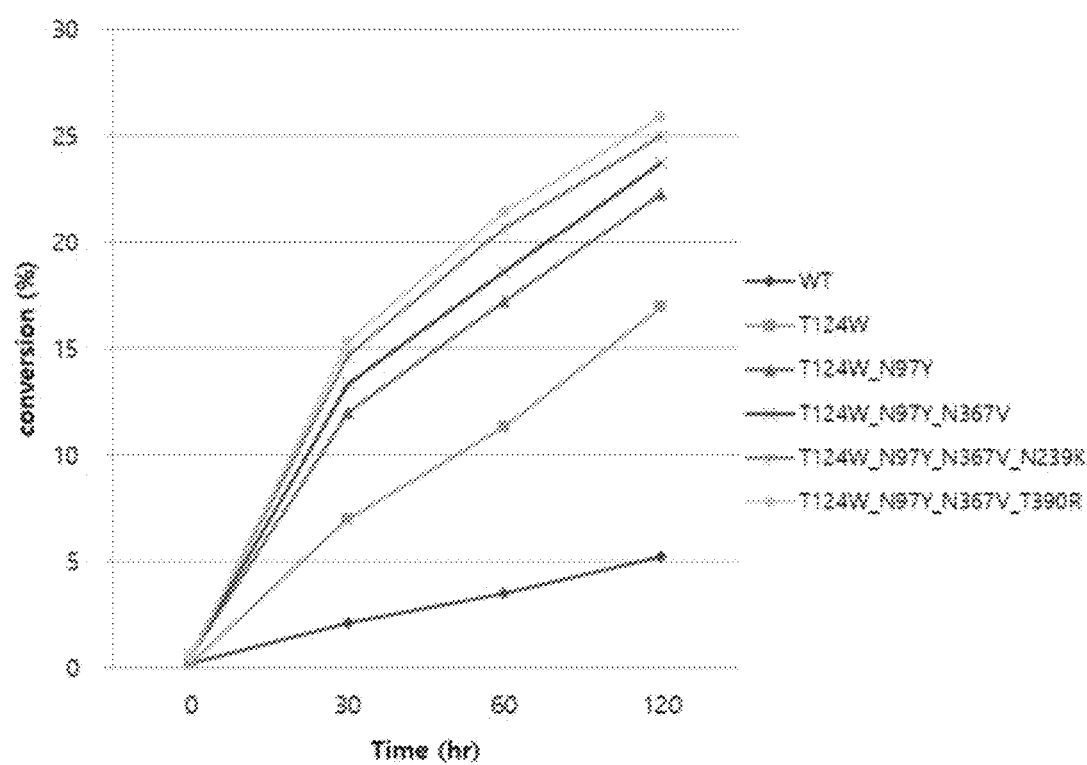

[FIG. 4]
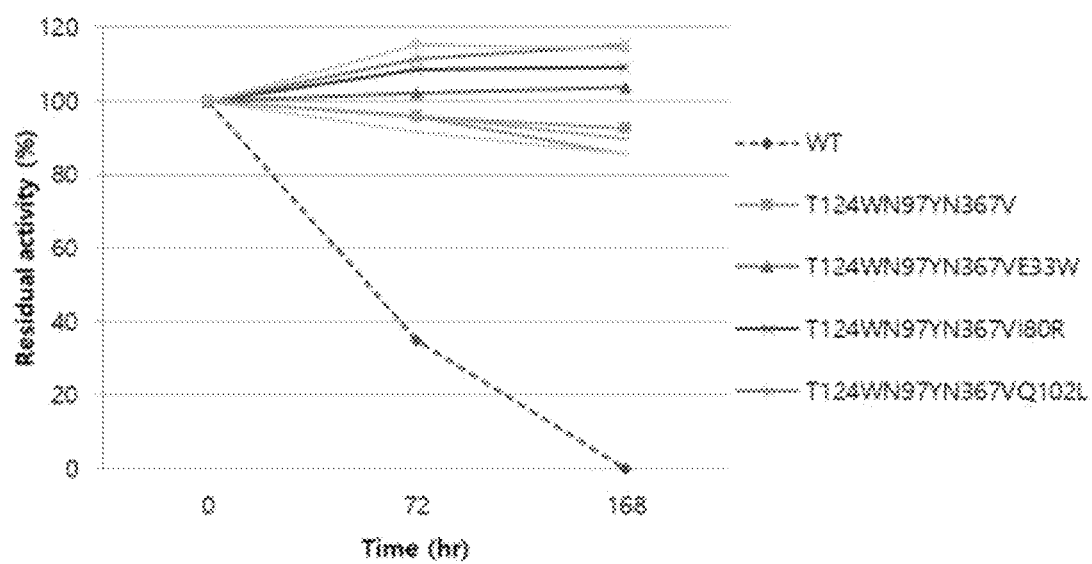

FRUCTOSE-4-EPIMERASE AND METHOD OF PREPARING TAGATOSE USING THE SAME

This application includes an electronically submitted sequence listing in .txt format. The .txt file contains a sequence listing entitled "059520_00022_ST25.txt" created on Mar. 26, 2021 and is 69 KB in size. The sequence listing contained in this .txt file is part of the specification and is hereby incorporated by reference herein in its entirety.

TECHNICAL FIELD

The present disclosure relates to a fructose-4-epimerase variant having improved conversion activity or stability, and a method of producing tagatose using the same.

BACKGROUND ART

Tagatose has a natural sweet taste hardly distinguishable from sucrose and also has physical properties similar to sucrose. Tagatose is a natural sweetener, which is present in a small amount in food such as milk, cheese, cacao, etc., and in sweet fruits such as apples and mandarin. Tagatose has a calorie value of 1.5 kcal/g which is one third that of sucrose, and a glycemic index (GI) of 3 which is 5% that of sucrose. Tagatose has a sweet taste similar to that of sucrose and various health benefits. In this regard, tagatose may be used as an alternative sweetener capable of satisfying both health and taste when applied to a wide variety of products.

Conventional known methods of producing tagatose include a chemical method (a catalytic reaction) and a biological method (an isomerizing enzyme reaction) of using galactose as a main raw material (see Korean Patent No. 10-0964091). In order to economically obtain galactose as a raw material for the above reactions, studies have been conducted on various basic raw materials containing galactose, and a method of obtaining galactose therefrom to produce tagatose. A representative basic raw material for obtaining galactose is lactose. However, the price of lactose or lactose-containing products was unstable, depending on produced amounts, supply and demand of raw milk and lactose in global markets, etc. Thus, there is a limitation in the stable supply of the raw material for tagatose production. Accordingly, there is a demand for a new method capable of producing tagatose using common saccharides (sucrose, glucose, fructose, etc.).

DISCLOSURE

Technical Problem

The present inventors have developed a novel variant protein including one or more amino acid substitutions in an amino acid sequence of SEQ ID NO: 1, and they found that the variant protein has conversion activity identical to that of the wild-type of SEQ ID NO: 1, or has improved conversion activity or stability and improved tagatose productivity, as compared with the wild-type, thereby completing the present disclosure.

Technical Solution

An object of the present disclosure is to provide a fructose-4-epimerase variant including one or more amino acid substitutions in an amino acid sequence of SEQ ID NO: 1.

Another object of the present disclosure is to provide a polynucleotide encoding the fructose-4-epimerase variant.

Still another object of the present disclosure is to provide a vector including the polynucleotide.

Still another object of the present disclosure is to provide a microorganism including the variant.

Still another object of the present disclosure is to provide a composition for producing tagatose, the composition including one or more of the fructose-4-epimerase variant; the microorganism expressing the variant; or a culture of the microorganism.

Still another object of the present disclosure is to provide a method of producing tagatose, the method including the step of reacting fructose in the presence of the microorganism; the culture thereof; or the fructose-4-epimerase derived therefrom.

Advantageous Effects

A fructose-4-epimerase variant of the present disclosure enables industrial scale production of tagatose having excellent characteristics, and converts fructose, which is a common saccharide, into tagatose, thereby exhibiting a high economical effect.

DESCRIPTION OF DRAWINGS

FIG. 1 shows HPLC chromatography results showing that tagatose-bisphosphate aldolase (KO_F4E) prepared in one embodiment of the present disclosure has fructose-4-epimerase activity;

FIG. 2 shows results of measuring thermal stability of variants at 60° C. over time, wherein the variants have variation of threonine at position 124 prepared in one embodiment of the present disclosure;

FIG. 3 shows results of measuring degree of activity over time under a temperature condition of 60° C., wherein the activity is fructose-4-epimerization activity of variants prepared in one embodiment of the present disclosure; and FIG. 4 shows results of measuring thermal stability at 60° C. over time, wherein the thermal stability is thermal stability of variants prepared in one embodiment of the present disclosure.

BEST MODE

The present disclosure will be described in detail as follows. Meanwhile, each description and embodiment disclosed in this disclosure may also be applied to other descriptions and embodiments. That is, all combinations of various elements disclosed in this disclosure fall within the scope of the present disclosure. Further, the scope of the present disclosure is not limited by the specific description described below.

To achieve the objects, one aspect of the present disclosure provides a fructose-4-epimerase variant including one or more amino acid substitutions in an amino acid sequence of fructose-4-epimerase.

To achieve the objects, another aspect of the present disclosure provides a fructose-4-epimerase variant including one or more amino acid substitutions in an amino acid sequence of SEQ ID NO: 1.

As used herein, the term "fructose-4-epimerase" is an enzyme having fructose-4-epimerization activity to convert fructose into tagatose by epimerization at C4 position of fructose. With respect to the objects of the present disclosure, fructose-4-epimerase may include any enzyme without limitation, as long as it is able to produce tagatose using fructose as a substrate, and it may be used interchangeably with 'D-fructose C4-epimerase'. For example, the fructose-4-epimerase may include tagatose bisphosphate aldolase or tagatose-bisphosphate aldolase class II accessory protein belonging to EC 4.1.2.40 in a known database KEGG (Kyoto Encyclopedia of Genes and Genomes), as long as it has activity to convert fructose as a substrate into tagatose. The tagatose-bisphosphate aldolase is known as an enzyme that produces glycerone phosphate and D-glyceraldehyde 3-phosphate from D-tagatose 1,6-bisphosphate as a substrate, as in the following [Reaction Scheme 1].

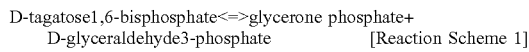
D-tagatose1,6-bisphosphate<=>glycerone phosphate+ D-glyceraldehyde3-phosphate    [Reaction Scheme 1]

For example, the fructose-4-epimerase may include tagatose-6-phosphate kinase (EC 2.7.1.144), as long as it has activity to convert fructose as a substrate into tagatose. The tagatose-6-phosphate kinase is known as an enzyme that produces ADP and D-tagatose 1,6-bisphosphate from ATP and D-tagatose 6-phosphate as a substrate, as in the following [Reaction Scheme 2].

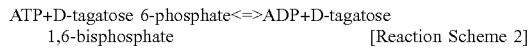
ATP+D-tagatose 6-phosphate<=>ADP+D-tagatose 1,6-bisphosphate    [Reaction Scheme 2]

The activity of fructose-4-epimerase may have a conversion rate of tagatose from fructose as a substrate (conversion rate=tagatose weight/initial fructose weight*100) of 0.01% or more, specifically 0.1% or more, and more specifically 0.3% or more. Much more specifically, the conversion rate may be in the range of 0.01% to 100% or in the range of 0.1% to 50%.

The fructose-4-epimerase, tagatose-bisphosphate aldolase, or tagatose-6-phosphate kinase of the present disclosure may be an enzyme derived from a heat-resistant microorganism or a variant thereof, for example, an enzyme derived from *Kosmotoga olearia*, *Thermanaerothrix daxensis*, *Rhodothermus profundi*, *Rhodothermus marinus*, *Limnochorda pilosa*, *Caldithrix abyssi*, *Caldilinea aerophila*, *Thermoanaerobacter thermohydrosulfuricus*, *Acidobacteriales bacterium*, *Caldicellulosiruptor kronotskyensis*, *Thermoanaerobacterium thermosaccharolyticum*, or *Pseudoalteromonas* sp. H103, or a variant thereof, but is not limited thereto, specifically, an enzyme derived from *Kosmotoga olearia* (SEQ ID NO: 1), *Thermoanaerobacterium thermosaccharolyticum* (SEQ ID NO: 3), *Pseudoalteromonas* sp. H103 (SEQ ID NO: 5), *Thermanaerothrix daxensis* (SEQ ID NO: 7), *Acidobacteriales bacterium* (SEQ ID NO: 9), *Rhodothermus profundi* (SEQ ID NO: 11), *Rhodothermus marinus* (SEQ ID NO: 13), *Limnochorda pilosa* (SEQ ID NO: 15), *Caldithrix abyssi* (SEQ ID NO: 17), *Caldicellulosiruptor kronotskyensis* (SEQ ID NO: 19), *Caldilinea aerophila* (SEQ ID NO: 21), or *Thermoanaerobacter thermohydrosulfuricus* (SEQ ID NO: 23), or a variant thereof, but is not limited thereto.

Specifically, the fructose-4-epimerase, tagatose-bisphosphate aldolase, or tagatose-6-phosphate kinase may include an amino acid sequence of SEQ ID NO: 1, 3, 5, 7, 9, 11, 13, 15, 17, 19, 21, or 23, or an amino acid sequence having 70% or higher homology or identity, but is not limited thereto. More specifically, the fructose-4-epimerase of the present disclosure may include a polypeptide having at least 60%, 70%, 80%, 85%, 90%, 95%, 96%, 97%, 98%, or 99% homology or identity to the amino acid sequence of SEQ ID NO: 1, 3, 5, 7, 9, 11, 13, 15, 17, 19, 21, or 23. Further, it is apparent that an accessory protein having an amino acid sequence having the homology or identity and exhibiting the efficacy corresponding to the above protein is also included in the scope of the present disclosure, although a partial sequence of the amino acid sequence is deleted, modified, substituted, or added.

In the present disclosure, SEQ ID NO: 1 means an amino acid sequence having fructose-4-epimerase activity. The sequence of SEQ ID NO: 1 may be obtained from a known database, GenBank of NCBI or KEGG (Kyoto Encyclopedia of Genes and Genomes). For example, the sequence may be derived from *Kosmotoga olearia*, more specifically, a polypeptide/protein including the amino acid sequence of SEQ ID NO: 1, but is not limited thereto. Further, a sequence having activity identical to the above amino acid sequence may be included without limitation. Further, the amino acid sequence of SEQ ID NO: 1 or an amino acid sequence having 70% or higher homology or identity thereto may be included, but is not limited thereto. Specifically, the amino acid sequence may include the amino acid sequence having SEQ ID NO: 1 and an amino acid sequence having at least 70%, 80%, 85%, 90%, 95%, 96%, 97%, 98%, or 99% or higher homology or identity to SEQ ID NO: 1. Further, it is apparent that a protein having an amino acid sequence having the homology or identity and exhibiting the efficacy corresponding to the above protein is also included in the scope of the present disclosure, although a partial sequence of the amino acid sequence is deleted, modified, substituted, or added.

That is, although described as "a protein having an amino acid sequence of a particular SEQ ID NO" in the present disclosure, the protein may have an activity that is identical or similar to that of a protein consisting of an amino acid sequence of the corresponding SEQ ID NO. In such a case, it is obvious that any proteins having an amino acid sequence with deletion, modification, substitution, conservative substitution, or addition in part of the sequence also can be used in the present disclosure. For example, in the case of having the activity that is the same as or corresponding to that of the modified protein, it does not exclude an addition of a sequence upstream or downstream of the amino acid sequence, which does not alter the function of the protein, a mutation that may occur naturally, a silent mutation thereof, or a conservative constitution, and even when the sequence addition or mutation is present, it obviously belongs to the scope of the present disclosure.

As used herein, the term "tagatose" is, a kind of ketohexose which is a monosaccharide, used interchangeably with "D-tagatose".

As used herein, the term "fructose-4-epimerase variant" means a fructose-4-epimerase variant including one or more amino acid substitutions in the amino acid sequence of the polypeptide having fructose-4-epimerase activity.

The fructose-4-epimerase variant may include one variation, two variations, three variations, four variations, or five variations including substitution of another amino acid for an amino acid at position 124 in the amino acid sequence of SEQ ID NO: 1, but is not limited thereto.

Specifically, provided is a fructose-4-epimerase variant including i) substitution of another amino acid for the amino acid at position 124, ii) substitution of another amino acids for amino acids at positions 124 and 390, iii) substitution of another amino acids for amino acids at positions 124 and 97, iv) substitution of another amino acids for amino acids at positions 124 and 97, and further substitution of another amino acid for any one of amino acids at positions 33, 80, 102, 137, 210, 318, and 367, v) substitution of another amino acids for amino acids at positions 124, 97, and 367, and further substitution of another amino acid for any one of amino acids at positions 33, 80, 102, 137, 210, 239, and 318, vi) substitution of another amino acids for amino acids at positions 124, 97, 367, and 33, and further substitution of another amino acid for any one of amino acids at positions 80, 102, 210, and 318, vii) substitution of another amino acids for amino acids at positions 124, 97, 367, and 80, and further substitution of another amino acid for any one of amino acids at positions 102, 137, and 210, or viii) substitution of another amino acids for amino acids at positions 124, 97, 367, 210, and 318, but is not limited thereto.

As used herein, 'position N' may include position N and an amino acid position corresponding to the position N, specifically, an amino acid position corresponding to any amino acid residue in a mature polypeptide disclosed in a particular amino acid sequence. The particular amino acid sequence may be any one of the amino acid sequences of SEQ ID NOS: 1, 3, 5, 7, 9, 11, 13, 15, 17, 19, 21, and 23.

The amino acid position corresponding to the position N or the amino acid position corresponding to any amino acid residue in the mature polypeptide disclosed in the particular amino acid sequence may be determined using the Needleman-Wunsch algorithm (literature [Needleman and Wunsch, 1970, J. Mol. Biol. 48: 443-453]), specifically, version 5.0.0 or later, as implemented in the Needle program of the EMBOSS package (EMBOSS: The European Molecular Biology Open Software Suite, literature [Rice et al., 2000, Trends Genet. 16:276-277]). Parameters used may be gap open penalty of 10, gap extension penalty of 0.5, and EBLOSUM62 (EMBOSS version of BLOSUM62) substitution matrix.

Identification of the amino acid residue at the amino acid position corresponding to the position N or at the amino acid position corresponding to any amino acid residue in the mature polypeptide disclosed in the particular amino acid sequence may be determined by alignment of multiple polypeptide sequences using several computer programs including, but not limited to, MUSCLE (multiple sequence comparison by log-expectation; version 3.5 or later; literature [Edgar, 2004, Nucleic Acids Research 32: 1792-1797]), MAFFT (version 6.857 or later; literature [Katoh and Kuma, 2002, Nucleic Acids Research 30: 3059-3066]; literature [Katoh et al., 2005, Nucleic Acids Research 33: 511-518]; literature [Katoh and Toh, 2007, Bioinformatics 23: 372-374]; literature [Katoh et al., 2009, Methods in Molecular Biology 537: 39-64]; literature [Katoh and Toh, 2010, Bioinformatics 26: 1899-1900]), and EMBOSS EMMA employing ClustalW (1.83 or later; literature [Thompson et al., 1994, Nucleic Acids Research 22: 4673-4680]), using their respective default parameters.

When the other polypeptide has diverged from the mature polypeptide of the particular amino acid sequence such that traditional sequence-based comparison fails to detect their relationship (literature [Lindahl and Elofsson, 2000, J. Mol. Biol. 295: 613-615]), other pairwise sequence comparison algorithms may be used. Greater sensitivity in sequence-based searching may be attained using search programs that utilize probabilistic representations of polypeptide families (profiles) to search databases. For example, PSI-BLAST program generates profiles through an iterative database search process and is capable of detecting remote homologs (literature [Atschul et al., 1997, Nucleic Acids Res. 25: 3389-3402]). Even greater sensitivity may be achieved if the family or superfamily for the polypeptide has one or more representatives in the protein structure databases. Programs such as GenTHREADER (literature [Jones, 1999, J. Mol. Biol. 287: 797-815]; literature [McGuffin and Jones, 2003, Bioinformatics 19: 874-881]) utilize information from a variety of sources (PSI-BLAST, secondary structure prediction, structural alignment profiles, and solvation potentials) as input to a neural network that predicts the structural folding for a query sequence. Similarly, the method of literature [Gough et al., 2000, J. Mol. Biol. 313: 903-919] may be used to align a sequence of unknown structure with the superfamily models present in the SCOP database. These alignments may in turn be used to generate homology, similarity, or identity models for the polypeptide, and such models may be assessed for accuracy using a variety of tools developed for that purpose.

The 'another polypeptide' is not limited, as long as it is an amino acid other than the amino acid corresponding to the position. 'Amino acids' are classified into four types of acidic, basic, polar (hydrophilic), and nonpolar (hydrophobic) amino acids according to properties of their side chains.

Specifically, the variant may be a protein having substitution of one or more amino acids selected from the group consisting of nonpolar amino acids including glycine (G), alanine (A), valine (V), leucine (L), isoleucine (I), methionine (M), phenylalanine (F), tryptophan (W), and proline (P); polar amino acids including serine (S), threonine (T), cysteine (C), tyrosine (Y), aspartic acid (D), and glutamine (Q); acidic amino acids including asparagine (N) and glutamic acid (E); and basic amino acids including lysine (K), arginine (R), and histidine (H) for an amino acid at each position of the amino acid sequence of SEQ ID NO: 1, but is not limited thereto.

Specifically, the variant may have substitution of a polar amino acid or nonpolar amino acid, except threonine (T), for the threonine (T) residue at position 124 from the N-terminus of the fructose-4-epimerase including the amino acid sequence of SEQ ID NO: 1, wherein the polar amino acid or nonpolar amino acid may be selected from the group consisting of tryptophan (W), cysteine (C), and tyrosine (Y), but is not limited thereto.

The variant having substitution of another amino acid for the threonine (T) residue at position 124 from the N-terminus of the fructose-4-epimerase including the amino acid sequence of SEQ ID NO: 1 may have further substitution of a nonpolar amino acid, acidic amino acid, or basic amino acid, except threonine (T), for the amino acid at position 390, wherein the nonpolar amino acid, acidic amino acid, or basic amino acid may be selected from the group consisting of lysine (K), glycine (G), valine (V), leucine (L), histidine (H), aspartic acid (D), isoleucine (I), and arginine (R), but is not limited thereto.

The variant having substitution of another amino acid for the threonine (T) residue at position 124 from the N-terminus of the fructose-4-epimerase including the amino acid sequence of SEQ ID NO: 1 may have further substitution of a polar amino acid, except asparagine (N), for the amino acid at position 97, wherein the polar amino acid may be tyrosine (Y), but is not limited thereto.

The variant having substitution of a polar amino acid or nonpolar amino acid, except threonine (T), for the threonine (T) residue at position 124 and substitution of a polar amino acid, except asparagine (N), for the amino acid at position 97 from the N-terminus of the fructose-4-epimerase including the amino acid sequence of SEQ ID NO: 1 may have further substitution of another amino acid for any one amino acid at positions 33, 80, 102, 137, 210, and 318, wherein the another amino acid may be selected from the group consisting of glycine (G), alanine (A), arginine (R), valine (V), leucine (L), isoleucine (I), threonine (T), proline (P), serine (S), tryptophan (W), phenylalanine (F), histidine (H), cysteine (C), tyrosine (Y), lysine (K), aspartic acid (D), and glutamic acid (E), but is not limited thereto. Specifically, the variant may have substitution of alanine (A), serine (S), tryptophan (W), glycine (G), phenylalanine (F), or tyrosine (Y) for the amino acid at position 33, substitution of phenylalanine (F), tyrosine (Y), arginine (R), phenylalanine (F), cysteine (C), threonine (T), serine (S), leucine (L), lysine (K), or glutamic acid (E) for the amino acid at position 80, substitution of threonine (T), alanine (A), proline (P), serine (S), leucine (L), isoleucine (I), or tryptophan (W) for the amino acid at position 102, substitution of cysteine (C), glutamic acid (E), glycine (G), arginine (R), or phenylalanine (F) for the amino acid at position 137, substitution of aspartic acid (D), serine (S), lysine (K), valine (V), leucine (L), or glycine (G) for the amino acid at position 210, substitution of histidine (H), glycine (G), isoleucine (I), alanine (A), or cysteine (C) for the amino acid at position 318, but is not limited thereto. The variant having substitution of a polar amino acid or nonpolar amino acid, except threonine (T), for the threonine (T) residue at position 124, substitution of a polar amino acid, except asparagine (N), for the amino acid at position 97, substitution of a polar amino acid, except threonine (T), for the amino acid at position 210, substitution of a basic amino acid, except threonine (T), for the amino acid at position 390 from the N-terminus of the fructose-4-epimerase including the amino acid sequence of SEQ ID NO: 1 may have further substitution of a nonpolar amino acid, except proline (P), for the amino acid at position 318, wherein the nonpolar amino acid may be glycine (G), but is not limited thereto.

The variant having substitution of a polar amino acid or nonpolar amino acid, except threonine (T), for the threonine (T) residue at position 124 from the N-terminus of the fructose-4-epimerase including the amino acid sequence of SEQ ID NO: 1 may have further substitution of a polar amino acid, except asparagine (N), for the amino acid at position 97, and substitution of a nonpolar amino acid, except asparagine (N), for the amino acid at position 367, wherein the polar amino acid may be tyrosine (Y) and the nonpolar amino acid may be valine (V), but is not limited thereto.

The variant having substitution of a polar amino acid or nonpolar amino acid, except threonine (T), for the threonine (T) residue at position 124, substitution of a polar amino acid, except asparagine (N), for the amino acid at position 97, and substitution of a nonpolar amino acid, except asparagine (N), for the amino acid at position 367 from the N-terminus of the fructose-4-epimerase including the amino acid sequence of SEQ ID NO: 1 may have further substitution of a nonpolar amino acid, polar amino acid, or basic amino acid for any one amino acid at positions 102, 137, 210, 239, and 318, wherein the nonpolar amino acid, polar amino acid, or basic amino acid may be selected from the group consisting of leucine (L), cysteine (C), serine (S), lysine (K), and glycine, (G), but is not limited thereto.

Specifically, the amino acid at position 102 may be substituted by leucine (L), the amino acid at position 137 may be substituted by cysteine (C), the amino acid at position 210 may be substituted by serine (S), the amino acid at position 239 may be substituted by lysine (K), or the amino acid at position 318 may be substituted by glycine (G), but is not limited thereto.

The variant having substitution of a polar amino acid or nonpolar amino acid, except threonine (T), for the threonine (T) residue at position 124, substitution of a polar amino acid, except asparagine (N), for the amino acid at position 97, and substitution of a nonpolar amino acid, except asparagine (N), for the amino acid at position 367 from the N-terminus of the fructose-4-epimerase including the amino acid sequence of SEQ ID NO: 1 may have further substitution of a nonpolar amino acid for the amino acid at position 33, wherein the nonpolar amino acid may be arginine (R), but is not limited thereto.

The variant having substitution of a polar amino acid or nonpolar amino acid, except threonine (T), for the threonine (T) residue at position 124, substitution of a polar amino acid, except asparagine (N), for the amino acid at position 97, substitution of a nonpolar amino acid, except asparagine (N), for the amino acid at position 367, and substitution of a nonpolar amino acid for the amino acid at position 33 from the N-terminus of the fructose-4-epimerase including the amino acid sequence of SEQ ID NO: 1 may have further substitution of a basic amino acid, nonpolar amino acid, or polar amino acid for any one amino acid at positions 80, 102, 210, and 318, wherein the basic amino acid, nonpolar amino acid, or polar amino acid may be selected from the group consisting of arginine (R), leucine (L), serine (S), and glycine (G), but is not limited thereto.

Specifically, the amino acid at position 80 may be substituted by arginine (R), the amino acid at position 102 may be substituted by leucine (L), the amino acid at position 210 may be substituted by serine (S), or the amino acid at position 318 may be substituted by glycine (G), but is not limited thereto.

The variant having substitution of a polar amino acid or nonpolar amino acid, except threonine (T), for the threonine (T) residue at position 124, substitution of a polar amino acid, except asparagine (N), for the amino acid at position 97, and substitution of a nonpolar amino acid, except asparagine (N), for the amino acid at position 367 from the N-terminus of the fructose-4-epimerase including the amino acid sequence of SEQ ID NO: 1 may have further substitution of a basic amino acid for the amino acid at position 80, wherein the basic amino acid may be arginine (R), but is not limited thereto.

The variant having substitution of a polar amino acid or nonpolar amino acid, except threonine (T), for the threonine (T) residue at position 124, substitution of a polar amino acid, except asparagine (N), for the amino acid at position 97, substitution of a nonpolar amino acid, except asparagine (N), for the amino acid at position 367, and substitution of a basic amino acid for the amino acid at position 80 from the N-terminus of the fructose-4-epimerase including the amino acid sequence of SEQ ID NO: 1 may have further substitution of a nonpolar amino acid or polar amino acid for any one amino acid at positions 102, 137, and 210, wherein the nonpolar amino acid or polar amino acid may be selected from the group consisting of leucine (L), cysteine (C), and serine (S), but is not limited thereto.

Specifically, the amino acid at position 102 may be substituted by leucine (L), the amino acid at position 137 may be substituted by cysteine (C), or the amino acid at position 210 may be substituted by serine (S), but is not limited thereto. The variant having substitution of a polar amino acid or nonpolar amino acid, except threonine (T), for the threonine (T) residue at position 124, substitution of a polar amino acid, except asparagine (N), for the amino acid at position 97, and substitution of a nonpolar amino acid, except asparagine (N), for the amino acid at position 367 from the N-terminus of the fructose-4-epimerase including the amino acid sequence of SEQ ID NO: 1 may have further substitution of a polar amino acid, except threonine (T), for the amino acid at position 210 and substitution of a nonpolar amino acid, except proline (P), for the amino acid at position 318, wherein the polar amino acid may be serine (S) and the nonpolar amino acid may be glycine (G), but is not limited thereto.

The fructose-4-epimerase variant may include a polypeptide, of which one or more amino acids differ from the recited sequence in conservative substitutions and/or modifications, in addition to substitution of another amino acid for the amino acid at the particular position, while retaining functions or properties of the protein.

As used herein, the term "conservative substitution" means substitution of one amino acid with another amino acid that has similar structural and/or chemical properties. The variant may have, for example, one or more conservative substitutions while retaining one or more biological activities. The conservative substitution has little or no impact on the activity of a resulting polypeptide Further, variants having variation of one or more amino acids in addition to the amino acids at the above-described particular positions may include deletion or addition of amino acids that have minimal influence on properties and a secondary structure of the polypeptide. For example, a polypeptide may be conjugated to a signal (or leader) sequence at the N-terminus of the protein, which co-translationally or post-translationally directs transfer of the protein. The polypeptide may also be conjugated to other sequence or a linker for identification, purification, or synthesis of the polypeptide.

Further, the variant includes the above-described variations of SEQ ID NO: 1 and/or amino acids having at least 70%, 80%, 85%, 90%, 95%, 96%, 97%, 98%, or 99% or higher homology or identity to SEQ ID NO: 1 other than the variations and positions of SEQ ID NO: 1. The variations of SEQ ID NO: 1 are as described above, and homology or identity thereto may be homology or identity at positions other than the above-described variations.

With respect to the objects of the present disclosure, the fructose-4-epimerase variant is characterized by having improved conversion activity or stability, as compared with the wild-type.

The term "conversion activity" means conversion into tagatose by epimerizing D-fructose at C4 position. The term "stability" means having thermal stability of an enzyme having high heat resistance. Specifically, the fructose-4-epimerase variant of SEQ ID NO: 1 is characterized in that its activity to convert into tagatose by epimerizing D-fructose at C4 position and/or thermal stability are/is improved, as compared with the wild-type of SEQ ID NO: 1.

For example, the fructose-4-epimerase variant of the present disclosure may be an enzyme having high heat resistance. Specifically, the fructose-4-epimerase variant of the present disclosure may exhibit 50% to 100%, 60% to 100%, 70% to 100%, or 75% to 100% activity of the maximum activity at 50° C. to 70° C. More specifically, the fructose-4-epimerase variant of the present disclosure may exhibit 80% to 100% or 85% to 100% activity of the maximum activity at 55° C. to 60° C., 60° C. to 70° C., 55° C., 60° C., or 70° C.

Another aspect of the present disclosure provides a polynucleotide encoding the fructose-4-epimerase variant, or a vector including the polynucleotide.

As used herein, the term "polynucleotide" refers to a DNA or RAN strand having a predetermined length or more, which is a long chain polymer of nucleotides formed by linking nucleotide monomers via covalent bonds. More specifically, the polynucleotide refers to a polynucleotide fragment encoding the variant protein.

The polynucleotide encoding the fructose-4-epimerase variant of the present disclosure may include any polynucleotide sequence without limitation, as long as it is a polynucleotide sequence encoding the fructose-4-epimerase variant of the present disclosure. For example, the polynucleotide encoding the fructose-4-epimerase variant of the present disclosure may be a polynucleotide sequence encoding the amino acid sequence, but is not limited thereto. In the polynucleotide, various modifications may be made in the coding region provided that they do not change the amino acid sequence of the protein, due to codon degeneracy or in consideration of the codons preferred by the organism in which the protein is to be expressed. Therefore, it is apparent that, due to codon degeneracy, a polynucleotide which may be translated into the polypeptide composed of the amino acid sequence or the polypeptide having homology or identity thereto may also be included.

Further, a probe which may be produced from a known nucleotide sequence, for example, a sequence which hybridizes with a complementary sequence to all or a part of the nucleotide sequence under stringent conditions to encode the fructose-4-epimerase variant may also be included without limitation.

The term "stringent conditions" mean conditions under which specific hybridization between polynucleotides is allowed. Such conditions are described in detail in a literature (e.g., J. Sambrook et al., supra). For example, the stringent conditions may include, for example, conditions under which genes having high homology or identity, 70% or higher, 80% or higher, 85% or higher, specifically 90% or higher, more specifically 95% or higher, much more specifically 97% or higher, particularly specifically 99% or higher homology or identity are hybridized with each other and genes having homology or identity lower than the above homology or identity are not hybridized with each other, or ordinary washing conditions of Southern hybridization, i.e., washing once, specifically, twice or three times at a salt concentration and a temperature corresponding to 60° C., 1×SSC, 0.1% SDS, specifically, 60° C., 0.1×SSC, 0.1% SDS, and more specifically 68° C., 0.1×SSC, 0.1% SDS.

Although a mismatch between nucleotides may occur due to the stringency of hybridization, it is required that the two nucleic acids have a complementary sequence. The term "complementary" is used to describe the relationship between nucleotide bases which may hybridize with each other. For example, with regard to DNA, adenosine is complementary to thymine and cytosine is complementary to guanine.

Accordingly, the present disclosure may include not only the substantially similar nucleic acid sequences but also isolated nucleic acid fragments which are complementary to the entire sequence.

Specifically, the polynucleotide having homology or identity may be detected using hybridization conditions including the hybridization step at a Tm value of 55° C. and the conditions described above. Additionally, the Tm value may be 60° C., 63° C., or 65° C., but is not limited thereto, and may be appropriately controlled by one of ordinary skill in the art according to the purposes.

Appropriate stringency for the hybridization of polynucleotides depends on the length and degree of complementarity of the polynucleotides, and the variables are well-known in the art (see Sambrook et al., supra, 9.50-9.51, 11.7-11.8).

As used herein, the term 'homology' or 'identity' means the degree of relevance between two given amino acid sequences or nucleotide sequences, and may be expressed as a percentage.

The terms 'homology' and 'identity' may be often used interchangeably.

The sequence homology or identity of the conserved polynucleotide or polypeptide may be determined by standard alignment algorithms, and may be used with default gap penalties established by the used program. Substantially, homologous or identical sequences may hybridize under moderately or highly stringent conditions such that the full length of the sequence or at least about 50%, 60%, 70%, 80%, or 90% or more of the full-length may hybridize. Also, contemplated are polynucleotides that contain degenerate codons in place of codons in the hybridization.

Whether or not any two polynucleotide or polypeptide sequences have homology, similarity, or identity may be determined using known computer algorithms such as the "FASTA" program, using, for example, the default parameters as in Pearson et al (1988)[Proc. Natl. Acad. Sci. USA 85]: 2444], or determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277) (version 5.0.0 or later) (including GCG program package (Devereux, J., et al, Nucleic Acids Research 12: 387 (1984)), BLASTP, BLASTN, FASTA (Atschul, [S.] [F.,] [ET AL, J MOLEC BIOL 215]: 403 (1990); Guide to Huge Computers, Martin J. Bishop, [ED.,] Academic Press, San Diego, 1994, and [CARILLO ETA/.] (1988) SIAM J Applied Math 48: 1073). For example, BLAST of the National Center for Biotechnology Information database, or ClustalW may be used to determine homology, similarity, or identity.

Homology, similarity, or identity of polynucleotides or polypeptides may be determined, for example, by comparing sequence information using a GAP computer program such as Needleman et al. (1970), J Mol Biol. 48: 443, as disclosed in Smith and Waterman, Adv. Appl. Math (1981) 2:482. Briefly, the GAP program defines similarity as the number of aligned symbols (i.e., nucleotides or amino acids), which are similar, divided by the total number of symbols in the shorter of the two sequences. Default parameters for the GAP program may include: (1) a binary comparison matrix (containing a value of 1 for identities and 0 for non-identities) and the weighted comparison matrix of Gribskov et al (1986) Nucl. Acids Res. 14: 6745, as disclosed in Schwartz and Dayhoff, eds., Atlas Of Protein Sequence And Structure, National Biomedical Research Foundation, pp. 353-358 (1979) (or EDNAFULL (EMBOSS version of NCBI NUC4.4) substitution matrix); (2) a penalty of 3.0 for each gap and an additional 0.10 penalty for each symbol in each gap (or gap open penalty of 10, gap extension penalty of 0.5); and (3) no penalty for end gaps. Therefore, as used herein, the term "homology" or "identity" represents relevance between sequences.

As used herein, the term "vector" means a DNA construct that includes a nucleotide sequence of a polynucleotide encoding a target variant protein operably linked to an appropriate regulatory sequence to enable expression of the target variant protein in an appropriate host cell. The regulatory sequence may include a promoter capable of initiating transcription, any operator sequence for the regulation of such transcription, a sequence of an appropriate mRNA ribosome-binding domain, and a sequence regulating termination of transcription and translation. After the vector is transformed into the appropriate host cell, it may replicate or function independently of the host genome, and may be integrated into the genome itself.

The vector used in the present disclosure is not particularly limited, as long as it is able to replicate in the host cell, and any vector known in the art may be used. Examples of commonly used vectors may include a natural or recombinant plasmid, cosmid, virus, and bacteriophage. For instance, pWE15, M13, MBL3, MBL4, IXII, ASHII, APII, t10, t11, Charon4A, Charon21A, etc. may be used as a phage vector or cosmid vector. As a plasmid vector, pBR type, pUC type, pBluescriptll type, pGEM type, pTZ type, pCL type, pET type, etc. may be used. Specifically, pDZ, pACYC177, pACYC184, pCL, pECCG117, pUC19, pBR322, pMW118, pCC1BAC vector, etc. may be used.

For example, a polynucleotide encoding a target variant protein in the chromosome may be replaced by a mutated polynucleotide using a vector for intracellular chromosomal insertion. The chromosomal insertion of the polynucleotide may be performed by any method known in the art, for example, homologous recombination, but is not limited thereto. A selection marker to confirm the chromosomal insertion may be further included. The selection marker is to select cells transformed with the vector, that is, to confirm insertion of the desired nucleotide molecule, and the selection marker may include markers providing selectable phenotypes, such as drug resistance, auxotrophy, resistance to cytotoxic agents, or expression of surface-modified proteins. Since only cells expressing the selection marker are able to survive or to show different phenotypes under the environment treated with a selective agent, the transformed cells may be selected. As still another aspect of the present disclosure, the present disclosure provides a microorganism producing tagatose, the microorganism including the variant protein or the polynucleotide encoding the variant protein. Specifically, the microorganism including the variant protein and/or the polynucleotide encoding the variant protein may be a microorganism prepared by transforming with the vector including the polynucleotide encoding the variant protein, but is not limited thereto.

As used herein, the term "transformation" means introduction of a vector including a polynucleotide encoding a target protein into a host cell in such a way that the protein encoded by the polynucleotide is expressed in the host cell. As long as the transformed polynucleotide may be expressed in the host cell, it may be integrated into and placed in the chromosome of the host cell, or it may exist extrachromosomally, or irrespective thereof. Further, the polynucleotide includes DNA and RNA encoding the target protein. The polynucleotide may be introduced in any form, as long as it may be introduced into the host cell and expressed therein. For example, the polynucleotide may be introduced into the host cell in the form of an expression cassette, which is a gene construct including all elements required for its autonomous expression. Commonly, the expression cassette includes a promoter operably linked to the polynucleotide, transcriptional termination signals, ribosome binding sites, and translation termination signals. The expression cassette may be in the form of a self-replicable expression vector. Also, the polynucleotide as it is may be introduced into the host cell and operably linked to sequences required for expression in the host cell, but is not limited thereto.

As used herein, the term "operably linked" means a functional linkage between a promoter sequence which initiates and mediates transcription of the polynucleotide encoding the target variant protein of the present disclosure and the polynucleotide sequence.

Still another aspect of the present disclosure provides a microorganism including the fructose-4-epimerase variant, the polynucleotide encoding fructose-4-epimerase variant, or the vector including the polynucleotide.

The microorganism may be a microorganism producing the fructose-4-epimerase variant or tagatose.

As used herein, the term "microorganism including the fructose-4-epimerase variant" may refer to a recombinant microorganism to express the fructose-4-epimerase variant of the present disclosure. For example, the microorganism refers to a host cell or a microorganism which is able to express the variant by including the polynucleotide encoding the fructose-4-epimerase variant or by transforming with the vector including the polynucleotide encoding the fructose-4-epimerase variant. With respect to the objects of the present disclosure, the microorganism is specifically a microorganism expressing the fructose-4-epimerase variant including one or more amino acid substitutions in the amino acid sequence of SEQ ID NO: 1, and the microorganism may be a microorganism expressing the variant protein having the fructose-4-epimerase activity, wherein the amino acid substitution is substitution of one or more amino acids at one or more positions from the N-terminus, but is not limited thereto.

The fructose-4-epimerase variant of the present disclosure may be obtained by transforming a microorganism such as *E. coli* with DNA expressing the enzyme of the present disclosure or the variant thereof, culturing the microorganism to obtain a culture, disrupting the culture, and then performing purification using a column, etc. The microorganism for transformation may include *Corynebacterium glutamicum*, *Aspergillus oryzae*, or *Bacillus subtilis*, in addition to *Escherichia coli*, but is not limited thereto.

The microorganism of the present disclosure may include either a prokaryotic microorganism or a eukaryotic microorganism, as long as it is a microorganism capable of producing the fructose-4-epimerase of the present disclosure by including the nucleic acid of the present disclosure or the recombinant vector of the present disclosure. For example, the microorganism may include microorganism strains belonging to the genus *Escherichia*, the genus *Erwinia*, the genus *Serratia*, the genus *Providencia*, the genus *Corynebacterium*, and the genus *Brevibacterium*, but is not limited thereto.

The microorganism of the present disclosure may include any microorganism capable of expressing the fructose-4-epimerase of the present disclosure by various known methods, in addition to introduction of the nucleic acid or the vector.

The culture of the microorganism of the present disclosure may be produced by culturing, in a medium, the microorganism capable of expressing the fructose-4-epimerase of the present disclosure.

In the method, the "culturing" means that the microorganism is allowed to grow under appropriately controlled environmental conditions. The step of culturing the microorganism may be, but is not particularly limited to, carried out by a known batch culture method, continuous culture method, or fed batch culture method. With regard to the culture conditions, a proper pH (e.g., pH 5 to 9, specifically pH 6 to 8, and most specifically pH 6.8) may be adjusted using a basic compound (e.g., sodium hydroxide, potassium hydroxide, or ammonia) or an acidic compound (e.g., phosphoric acid or sulfuric acid), but is not particularly limited thereto. Oxygen or an oxygen-containing gas mixture may be injected into the culture to maintain aerobic conditions. The culture temperature may be maintained from 20° C. to 45° C., and specifically, from 25° C. to 40° C. for about 10 hours to about 160 hours, but is not limited thereto.

Furthermore, the culture medium to be used may include, as carbon sources, sugars and carbohydrates (e.g., glucose, sucrose, lactose, fructose, maltose, molasse, starch, and cellulose), oil and fat (e.g., soybean oil, sunflower seed oil, peanut oil, and coconut oil), fatty acids (e.g., palmitic acid, stearic acid, and linoleic acid), alcohols (e.g., glycerol and ethanol), and organic acids (e.g., acetic acid) individually or in combination, but is not limited thereto. As nitrogen sources, nitrogen-containing organic compounds (e.g., peptone, yeast extract, meat broth, malt extract, corn steep liquor, soybean meal, and urea), or inorganic compounds (e.g., ammonium sulfate, ammonium chloride, ammonium phosphate, ammonium carbonate, and ammonium nitrate) may be used individually or in combination, but are not limited thereto. As phosphorus sources, dipotassium hydrogen phosphate, potassium dihydrogen phosphate, and corresponding sodium salts thereof may be used individually or in combination, but are not limited thereto. Further, the medium may include essential growth-stimulating substances including other metal salts (e.g., magnesium sulfate or iron sulfate), amino acids, and vitamins.

Still another aspect of the present disclosure provides a composition for producing tagatose, the composition including the fructose-4-epimerase variant; the microorganism expressing the same; or the culture of the microorganism.

The composition for producing tagatose of the present disclosure may further include fructose.

In addition, the composition for producing tagatose of the present disclosure may further include any appropriate excipient commonly used in the corresponding composition for producing tagatose. The excipient may include, for example, a preservative, a wetting agent, a dispersing agent, a suspending agent, a buffer, a stabilizer, an isotonic agent, etc., but is not limited thereto.

The composition for producing tagatose of the present disclosure may further include a metal ion or a metal salt. In a specific embodiment, a metal of the metal ion or the metal salt may be a metal containing a divalent cation. Specifically, the metal of the present disclosure may be nickel (Ni), iron (Fe), cobalt (Co), magnesium (Mg), or manganese (Mn). More specifically, the metal salt may be $MgSO_4$, $FeSO_4$, $NiSO_4$, $NiCl_2$, $MgCl_2$, $CoSO_4$, $MnCl_2$, or $MnSO_4$.

Still another aspect of the present disclosure provides a method of producing tagatose, the method including the step of converting fructose into tagatose by contacting fructose with the fructose-4-epimerase variant; the microorganism including the fructose-4-epimerase variant; or the culture thereof, specifically, a method of producing tagatose from fructose using the fructose-4-epimerase variant as a fructose-4-epimerase.

For example, the contacting of the present disclosure may be performed under a condition of pH 5.0 to pH 9.0, a temperature condition of 30° C. to 80° C., and/or for 0.5 hr to 48 hr.

Specifically, the contacting of the present disclosure may be performed under a condition of pH 6.0 to pH 9.0 or pH 7.0 to pH 9.0. Further, the contacting of the present disclosure may be performed under a temperature condition of 35° C. to 80° C., 40° C. to 80° C., 45° C. to 80° C., 50° C. to 80° C., 55° C. to 80° C., 60° C. to 80° C., 30° C. to 70° C., 35° C. to 70° C., 40° C. to 70° C., 45° C. to 70° C., 50° C. to 70° C., 55° C. to 70° C., 60° C. to 70° C., 30° C. to 65° C., 35° C. to 65° C., 40° C. to 65° C., 45° C. to 65° C., 50°

C. to 65° C., 55° C. to 65° C., 30° C. to 60° C., 35° C. to 60° C., 40° C. to 60° C., 45° C. to 60° C., 50° C. to 60° C. or 55° C. to 60° C. Further, the contacting of the present disclosure may be performed for 0.5 hr to 36 hr, 0.5 hr to 24 hr, 0.5 hr to 12 hr, 0.5 hr to 6 hr, 1 hr to 48 hr, 1 hr to 36 hr, 1 hr to 24 hr, 1 hr to 12 hr, 1 hr to 6 hr, 3 hr to 48 hr, 3 hr to 36 hr, 3 hr to 24 hr, 3 hr to 12 hr, 3 hr to 6 hr, 6 hr to 48 hr, 6 hr to 36 hr, 6 hr to 24 hr, 6 hr to 12 hr, 12 hr to 48 hr, 12 hr to 36 hr, 12 hr to 24 hr, 18 hr to 48 hr, 18 hr to 36 hr, or 18 hr to 30 hr.

Further, the contacting of the present disclosure may be performed in the presence of a metal ion or a metal salt. The applicable metal ion or metal salt is the same as described above.

The production method of the present disclosure may further include the step of separating and/or purifying the produced tagatose. The separation and/or purification may be performed using a method commonly used in the art. Non-limiting examples may include dialysis, precipitation, adsorption, electrophoresis, ion exchange chromatography, fractional crystallization, etc. The purification may be performed only by a single method or by two or more methods in combination.

In addition, the production method of the present disclosure may further include the step of performing decolorization and/or deionization, before or after the separation and/or purification step(s). By performing the decolorization and/or deionization, it is possible to obtain tagatose with higher quality.

For another example, the production method of the present disclosure may further include the step of performing crystallization of tagatose, after the step of converting into tagatose of the present disclosure, performing the separation and/or purification, or performing the decolorization and/or deionization. The crystallization may be performed by a crystallization method commonly used. For example, the crystallization may be performed by cooling crystallization.

Further, the production method of the present disclosure may further include the step of concentrating tagatose, before the step of performing crystallization. The concentrating may increase the crystallization efficiency.

For another example, the production method of the present disclosure may further include the step of contacting unreacted fructose with the enzyme of the present disclosure, the microorganism expressing the enzyme, or the culture of the microorganism after the step of separation and/or purification, or the step of reusing a crystal-separated mother solution in the step of separation and/or purification after the step of performing the crystallization of the present disclosure, or a combination thereof. The additional steps are economically advantageous in that tagatose may be obtained with higher yield and the amount of fructose to be discarded may be reduced.

MODE FOR INVENTION

Hereinafter, the present disclosure will be described in more detail with reference to Examples. However, these Examples are for the purpose of illustrating the present disclosure, and the scope of the present disclosure is not intended to be limited by these Examples. It will be apparent to those skilled in the art to which the present disclosure pertains.

Example 1. Preparation of Recombinant Expression Vectors and Transformants, Each Including Wild-Type Fructose-4-Epimerase Gene or Improved Fructose-4-Epimerase Gene Example 1-1. Preparation of Recombinant Expression Vectors and Transformants, Each Including Fructose-4-Epimerase Wild-Type Gene To prepare fructose-4-epimerase, *Kosmotoga olearia*-derived amino acid sequence (SEQ ID NO: 1) and genetic information were obtained to prepare a vector expressible in *E. coli* and a transformed microorganism (transformant). It was confirmed that the sequence may be used as a fructose-4-epimerase to convert fructose into tagatose (FIG. 1).

In detail, a nucleotide sequence of fructose-4-epimerase was selected from nucleotide sequences of *Kosmotoga olearia*, which is registered in KEGG (Kyoto Encyclopedia of Genes and Genomes). Based on the information of the amino acid sequence (SEQ ID NO: 1) and nucleotide sequence (SEQ ID NO: 2) of *Kosmotoga olearia*, it was inserted into pBT7-C-His which is a vector expressible in *E. coli* to synthesize and prepare a recombinant expression vector pBT7-C-His-KO, performed by Bioneer Corp.

Example 1-2. Preparation of Improved Fructose-4-Epimerase Library and Screening of Activity-Improved Variant Random mutation was performed using *Kosmotoga olearia*-derived fructose-4-epimerase gene as a template to construct a fructose-4-epimerase variant library. In detail, random mutation was induced using a diversify random mutagenesis kit (ClonTech) to generate 2 to 3 variations per 1000 base pairs in the fructose-4-epimerase gene. PCR reaction conditions are shown in the following Tables 1 and 2. The gene library encoding the fructose-4-epimerase variant was constructed and inserted into *E. coli* BL21(DE3).

TABLE 1

| Composition of reaction solution | Addition amount (μl) |
|---|---|
| PCR Grade Water | 36 |
| 10X TITANIUM Taq Buffer | 5 |
| MnSO4 (8 mM) | 4 |
| dGTP (2 mM) | 1 |
| 50X Diversify dNTP Mix | 1 |
| Primer mix | 1 |
| Template DNA | 1 |
| TITANIUM Taq Polym. | 1 |

TABLE 2

| Step | Temperature (° C.) | Time (sec) | Cycle |
|---|---|---|---|
| Initial Denaturation | 94 | 30 | 1 |
| Denaturation | 94 | 30 | 25 |
| Annealing/Extension | 68 | 60 | |
| Final Extension | 68 | 60 | 1 |
| soak | 4 | — | |

*E. coli* BL21(DE3) having the pBT7-C-His plasmid harboring the fructose-4-epimerase variant gene was seeded in a deep well rack containing 0.2 mL of an LB liquid medium supplemented with an ampicillin antibiotic, and seed-cultured in a shaking incubator at 37° C. for 16 hours or longer. The culture broth obtained from the seed culture was seeded in a culture deep well rack containing a liquid medium containing LB and lactose which is a protein expression regulator, followed by main culture. The seed culture and main culture were performed under conditions of a shaking speed of 180 rpm and 37° C. Next, the culture broth was centrifuged at 4,000 rpm and 4° C. for 20 minutes, and then the microorganism was recovered and subjected to an activity test.

For high-speed screening of a large amount of the activity-improved variant enzyme from the prepared random mutation library, a colorimetric method capable of specifically quantifying D-fructose was used. In detail, a 70% folin-ciocalteu reagent (SIGMA-ALDRICH) and a substrate reaction solution were mixed at a ratio of 15:1, and allowed to react at 80° C. for 5 minutes. OD values were measured at 900 nm to select variants having the activity (conversion of D-fructose into D-tagatose) by comparing the relative activity thereof with that of the wild-type enzyme (SEQ ID NO: 1). Among them, 30 colonies having the highest activity were selected, and sequenced to examine their base sequences. As a result, variations at positions 33, 80, 97, 102, 124, 137, 210, 239, 318, 367, and 390 were found. Through random mutation screening, T124W and N97Y which are variants having the most excellent activity were obtained.

Example 2. Preparation of Variant Enzymes and Comparative Evaluation of Activity To evaluate the relative fructose-4-epimerization activity of the excellent variants obtained in Example 1-2, the variant microorganisms were seeded in a culture tube containing 5 mL of an LB liquid medium supplemented with an ampicillin antibiotic, and seed-cultured in a shaking incubator at 37° C. until absorbance at 600 nm reached 2.0. The culture broth obtained from the seed culture was seeded in a culture flask containing a liquid medium containing LB and lactose which is a protein expression regulator, followed by main culture. The seed culture and main culture were performed under conditions of a shaking speed of 180 rpm and 37° C.

Next, the culture broth was centrifuged at 8,000 rpm 4° C. for 20 minutes, and then the microorganism was recovered. The recovered microorganism was washed with a 50 mM Tris-HCl (pH 8.0) buffer solution twice, and resuspended in a 50 mM $NaH_2PO_4$ (pH 8.0) buffer solution containing 10 mM imidazole and 300 mM NaCl. The resuspended microorganism was disrupted using a sonicator, and centrifuged at 13,000 rpm and 4° C. for 20 minutes to collect only the supernatant. The supernatant was purified using His-taq affinity chromatography, and a 50 mM $NaH_2PO_4$ (pH 8.0) buffer solution containing 20 mM imidazole and 300 mM NaCl was applied in a 10-fold volume of a filler to remove non-specific binding proteins. Subsequently, 50 mM $NaH_2PO_4$ (pH 8.0) buffer solution containing 250 mM imidazole and 300 mM NaCl was further applied to perform elution and purification. Then, dialysis was performed using a 50 mM Tris-HCl (pH 8.0) buffer solution, and the respective purified enzymes were obtained for characterization of the enzymes.

To measure the fructose-4-epimerization activity of the obtained purified enzymes, 50 mM Tris-HCl (pH 8.0), 3 mM $MnSO_4$, and each 10 mg/mL of the enzymes was added to 30% by weight of fructose, and allowed to react at 60° C. for up to 2 hours. As a result, it was confirmed that the conversion activity of the wild-type (KO) was 8.6%, and the conversion activity of the variant enzyme N97Y was 21.5%, the conversion activity of the variant enzyme T124W was 25.3%. In other words, it was found that the activity of the variant enzymes was increased, as compared with that of the wild-type.

Example 3. Preparation of Variant Enzymes and Selection of Activity-Improved Variant Enzymes To examine the activity of the enzyme, in which a nonpolar or polar side chain other than threonine was substituted for threonine (T) at position 124 among target positions designed in Example 1-2, a single-site saturation mutagenesis library having substitution of tryptophan (W), cysteine (C), or tyrosine (Y) for threonine (T) at position 124 was constructed to prepare variant enzymes, and unit activity for the fructose-4-epimerization conversion was measured.

Example 3-1. Saturation Mutagenesis

The recombinant expression vector pBT7-C-His-KO which was prepared for expressing the wild-type enzyme gene in E. coli BL21(DE3) (expressing the recombinant enzyme having 6×His-tag at the C-terminus of the wild-type) was used as a template for saturation mutagenesis for variant library construction. In view of mutation frequency variation and variant yield, etc., inversed PCR-based saturation mutagenesis was used (2014. Anal. Biochem. 449: 90-98), and in order to minimize screening scales of the constructed variant library (minimize the number of codons introduced for saturation mutagenesis), a mixed primer NDT/VMA/ATG/TGG (2012. Biotechniques 52:149-158) in which stop codons were excluded and rare codons for E. coli were minimized was designed and used. In detail, a primer having a total length of 33 bp was constructed using 15 bp residing at the front side, 3 bp to be substituted, and 15 bp residing at the rear side of each site. PCR was performed by repeating cycles consisting of denaturing at 94° C. for 2 minutes, denaturing at 94° C. from 30 seconds, annealing at 60° C. for 30 seconds, and extending at 72° C. for 10 minutes, followed by elongation at 72° C. for 60 minutes. After construction of a saturation mutagenesis library for the selected amino acid sites, variants for each library were randomly selected (<11 variations). Base sequences were analyzed to evaluate amino acid mutation frequency. Based on the analysis results, scales of screening each library were set with sequence coverage of 90% or more (2003. Nucleic Acids Res. 15; 31:e30).

Example 3-2. Preparation of Activity-Improved Variant Enzymes

In order to evaluate relative activity of fructose-4-epimerization for a variant enzyme at a single site with improved unit activity and a variant enzyme at multiple sites with combination thereof, the saturation mutagenesis library gene prepared in 3-1 was transformed into E. coli BL21 (DE3), and each transformed microorganism was seeded in a culture tube containing 5 mL of LB liquid medium containing an ampicillin antibiotic, and seed-cultured in a shaking incubator at 37° C. until absorbance at 600 nm reached 2.0. The culture broth obtained from the seed culture was seeded in a culture flask containing a liquid medium containing LB and lactose which is a protein expression regulator, followed by main culture. The seed culture and main culture were performed under conditions of a shaking speed of 180 rpm and 37° C. Next, the culture broth was centrifuged at 8,000 rpm and 4° C. for 20 minutes, and then the microorganism was recovered. The recovered microorganism was washed with a 50 mM Tris-HCl (pH 8.0) buffer solution twice, and resuspended in a 50 mM NaH$_2$PO$_4$ (pH 8.0) buffer solution containing 10 mM imidazole and 300 mM NaCl. The resuspended microorganism was disrupted using a sonicator, and centrifuged at 13,000 rpm and 4° C. for 20 minutes to collect only the supernatant. The supernatant was purified using His-taq affinity chromatography, and a 50 mM NaH$_2$PO$_4$ (pH 8.0) buffer solution containing 20 mM imidazole and 300 mM NaCl was applied in a 10-fold volume of a filler to remove non-specific binding proteins. Subsequently, 50 mM NaH$_2$PO$_4$ (pH 8.0) buffer solution containing 250 mM imidazole and 300 mM NaCl was further applied to perform elution and purification. Then, dialysis was performed using a 50 mM Tris-HCl (pH 8.0) buffer solution, and the respective purified enzymes were obtained for characterization of the enzymes.

Example 3-3. Comparative Evaluation of Characteristics of Variant Enzymes

To measure the fructose-4-epimerization activity of the recombinant variant enzymes obtained in Example 3-2, 50 mM Tris-HCl (pH 8.0), 3 mM MnSO$_4$, and each 10 mg/mL of the enzymes was added to 30% by weight of fructose, and allowed to react at 60° C. for 2 hours. Furthermore, to measure thermal stability of the obtained recombinant variant enzymes, each enzyme purified at a concentration of 10 mg/mL was added and left at 60° C. for at least 19 hours and up to 90 hours, and then left on ice for 5 minutes. Each of the enzyme solutions sampled at each time point, 50 mM Tris-HCl (pH 8.0), and 3 mM MnSO$_4$ were added to 30% by weight of fructose, and an enzymatic reaction was allowed to measure residual activity of the enzymes.

As a result, all the prepared variants showed high conversion rates of up to 2.9 times that of the wild-type. Detailed results are shown in the following Table 3. Furthermore, the results of examining thermal stability showed that the fructose-4-epimerase variants showed reduction in the residual activity at 60° C. over time, but the thermal stability was more excellent than that of the wild-type, as shown in FIG. 2.

TABLE 3

|  | Variation site | | | |
| --- | --- | --- | --- | --- |
|  | T124W | T124C | T124Y | KO |
| Relative activity (%) | 294 | 245 | 251 | 100 |

Example 4. Preparation of Recombinant Variant Enzymes and Evaluation of Activity-Improved Variant Enzymes

Example 4-1. Site-Directed Mutagenesis

The variant T124W selected in Example 1-2 was used to substitute tyrosine for asparagine at position 97 of *Kosmotoga olearia*-derived fructose-4-epimerase using particular primers by site-directed mutagenesis.

An N-terminal primer (SEQ ID NO: 25: GACCATCTTGGCCCATACCCCTGGAAGGGTCAG) and a C-terminal primer (SEQ ID NO: 26: CTGACCCTTCCAGGGGTATGGGCCAAGATGGTC) which are oligonucleotides of two complementary base sequences having mutations were used as primers. A plasmid having a new variation was amplified and synthesized in a tube using DNA in the form of plasmid as a template, and the original template DNA was digested with a restriction enzyme Dpn I, and removed. In other words, the variant DNA selected in Example 1-2, which was used as the template, was DNA isolated from *E. coli*, which is digested with Dpn I recognizing and cleaving Gm6 ATC, but the variant DNA synthesized in the tube is not cleaved thereby. This was transformed into *E. coli* DH5alpha to obtain a variant strain. Sequencing analysis of the variant gene was performed to confirm that the variation properly occurred. In other words, T124W N97Y variant having the amino acid sequence variation was prepared. This variant was transformed into an expression strain *E. coli* BL21(DE3) to prepare a recombinant strain.

Example 4-2. Preparation of Activity-Improved Variant Enzymes and Comparative Evaluation of Activity The variant microorganism prepared in Example 4-1 was seeded in a culture tube containing 5 mL of LB liquid medium containing an ampicillin antibiotic, and seed-cultured in a shaking incubator at 37° C. until absorbance at 600 nm reached 2.0. The culture broth obtained from the seed culture was seeded in a culture flask containing a liquid medium containing LB and lactose which is a protein expression regulator, followed by main culture. The seed culture and main culture were performed under conditions of a shaking speed of 180 rpm and 37° C. Next, the culture broth was centrifuged at 8,000 rpm and 4° C. for 20 minutes, and then the microorganism was recovered. The recovered microorganism was washed with a 50 mM Tris-HCl (pH 8.0) buffer solution twice, and resuspended in a 50 mM NaH$_2$PO$_4$ (pH 8.0) buffer solution containing 10 mM imidazole and 300 mM NaCl.

The resuspended microorganism was disrupted using a sonicator, and centrifuged at 13,000 rpm and 4° C. for 20 minutes to collect only the supernatant. The supernatant was purified using His-taq affinity chromatography, and a 50 mM NaH$_2$PO$_4$ (pH 8.0) buffer solution containing 20 mM imidazole and 300 mM NaCl was applied in a 10-fold volume of a filler to remove non-specific binding proteins. Subsequently, 50 mM NaH$_2$PO$_4$ (pH 8.0) buffer solution containing 250 mM imidazole and 300 mM NaCl was further applied to perform elution and purification. Then, dialysis was performed using a 50 mM Tris-HCl (pH 8.0) buffer solution, and the purified enzymes were obtained for characterization of the enzymes.

To measure the fructose-4-epimerization activity of the obtained recombinant variant enzymes, 50 mM Tris-HCl (pH 8.0), 3 mM MnSO$_4$, and each 2 mg/mL of the enzymes were added to 30% by weight of fructose, and allowed to react at 60° C. for 2 hours.

As a result, all of the prepared variants showed high conversion rates of up to 4 times that of the wild-type. The detailed results are shown in the following Table 4.

TABLE 4

|  | 0 | 30 | 60 | 120 |
| --- | --- | --- | --- | --- |
| WT | 0.3 | 2.1 | 3.5 | 5.2 |
| T124W | 0.3 | 7.0 | 11.3 | 16.9 |
| T124W_N97Y | 0.5 | 12.0 | 17.2 | 22.2 |

Example 4-3. Preparation and Selection of Additional Recombinant Variant Enzymes To examine enzyme activity when various variations were added based on the variation at position 124, the following additional experiment was performed. In detail, 124W variant prepared in Example 1-2 and T124W N97Y variant prepared in Example 4-1 (substitution of tryptophan (W) for threonine (T) at position 124, and substitution of tyrosine (Y) for asparagine (N) at position 97, respectively) were used to construct a single-site saturation mutagenesis library based on 9 active sites selected through the random mutation library screening in Example 1-2 (at positions 33, 80, 102, 137, 210, 239, 318, 367, and 390). The variation sites and amino acids having improved unit activity were selected by screening. 63 kinds of variant enzymes with additional variation sites were obtained, as in Table 5. The kind of variation at each site is as in Table 6.

TABLE 5

| | Variation site | | | | | | | | | | |
|---|---|---|---|---|---|---|---|---|---|---|---|
| | 124 | 97 | 239 | 367 | 390 | 33 | 80 | 102 | 137 | 210 | 318 |
| Existing sequence | T | N | N | N | T | E | I | Q | D | T | P |
| M1 | W | | | | K | | | | | | |
| M2 | W | | | | G | | | | | | |
| M3 | W | | | | V | | | | | | |
| M4 | W | | | | L | | | | | | |
| M5 | W | | | | H | | | | | | |
| M6 | W | | | | D | | | | | | |
| M7 | W | | | | I | | | | | | |
| M8 | W | | | | R | | | | | | |
| M9 | W | Y | | | | A | | | | | |
| M10 | W | Y | | | | S | | | | | |
| M11 | W | Y | | | | W | | | | | |
| M12 | W | Y | | | | G | | | | | |
| M13 | W | Y | | | | F | | | | | |
| M14 | W | Y | | | | Y | | | | | |
| M15 | W | Y | | | | | W | | | | |
| M16 | W | Y | | | | | Y | | | | |
| M17 | W | Y | | | | | R | | | | |
| M18 | W | Y | | | | | F | | | | |
| M19 | W | Y | | | | | C | | | | |
| M20 | W | Y | | | | | T | | | | |
| M21 | W | Y | | | | | S | | | | |
| M22 | W | Y | | | | | L | | | | |
| M23 | W | Y | | | | | K | | | | |
| M24 | W | Y | | | | | E | | | | |
| M25 | W | Y | | | | | | T | | | |
| M26 | W | Y | | | | | | A | | | |
| M27 | W | Y | | | | | | S | | | |
| M28 | W | Y | | | | | | P | | | |
| M29 | W | Y | | | | | | W | | | |
| M30 | W | Y | | | | | | L | | | |
| M31 | W | Y | | | | | | I | | | |
| M32 | W | Y | | | | | | | C | | |
| M33 | W | Y | | | | | | | E | | |
| M34 | W | Y | | | | | | | G | | |
| M35 | W | Y | | | | | | | R | | |
| M36 | W | Y | | | | | | | F | | |
| M37 | W | Y | | | | | | | | D | |
| M38 | W | Y | | | | | | | | S | |
| M39 | W | Y | | | | | | | | K | |
| M40 | W | Y | | | | | | | | L | |
| M41 | W | Y | | | | | | | | V | |
| M42 | W | Y | | | | | | | | G | |
| M43 | W | Y | | | | | | | | | H |
| M44 | W | Y | | | | | | | | | G |
| M45 | W | Y | | | | | | | | | I |
| M46 | W | Y | | | | | | | | | A |
| M47 | W | Y | | | | | | | | | C |
| M48 | W | Y | | V | | | | | | | |
| M49 | W | Y | | V | | W | | | | | |
| M50 | W | Y | | V | | | R | | | | |
| M51 | W | Y | | V | | | | L | | | |
| M52 | W | Y | | V | | | | | C | | |
| M53 | W | Y | | V | | | | | | S | |
| M54 | W | Y | | V | | | | | | | G |
| M55 | W | Y | K | V | | | | | | | |
| M56 | W | Y | | V | | W | R | | | | |
| M57 | W | Y | | V | | W | | L | | | |
| M58 | W | Y | | V | | W | | | | S | |
| M59 | W | Y | | V | | W | | | | | G |
| M60 | W | Y | | V | | | R | L | | | |
| M61 | W | Y | | V | | | R | | C | | |
| M62 | W | Y | | V | | | R | | | S | |
| M63 | W | Y | | V | | | | | | S | G |

TABLE 6

| Variation site | | | | | | | | | | |
|---|---|---|---|---|---|---|---|---|---|---|
| E33 | A | S | W | G | F | Y | | | | |
| I80 | W | Y | R | F | C | T | S | L | K | E |
| Q102 | T | A | S | P | W | L | I | | | |
| D137 | C | E | G | R | F | | | | | |
| T210 | D | S | K | L | V | G | | | | |
| N239 | K | | | | | | | | | |
| P318 | H | G | I | A | C | | | | | |
| N367 | | | | | V | | | | | |
| T390 | K | G | V | L | H | D | I | R | | |

Example 5. Comparative Evaluation of Characteristics of Variant Enzymes

Example 5-1. Evaluation of Activity

To measure the fructose-4-epimerization activity of the recombinant variant enzymes obtained in Example 5, 50 mM Tris-HCl (pH 8.0), 3 mM MnSO$_4$, and each 2 mg/mL of the enzymes were added to 30% by weight of fructose, and allowed to react at 60° C. for 2 hours.

As a result, all of the variants showed increased fructose-4-epimerization activity, as compared with the conversion activity of the wild-type (KO). The detailed results are shown in the following Tables 7 to 9.

TABLE 7

| Variation site | Relative activity (%) |
|---|---|
| KO (WILD) | 100 |
| T124W | 412 |
| T124W + T390K | 604 |
| T124W + T390G | 460 |
| T124W + T390V | 496 |
| T124W + T390L | 452 |
| T124W + T390H | 504 |
| T124W + T390D | 352 |
| T124W + T390I | 432 |
| T124W + T390R | 668 |

TABLE 8

| Variation site | Additional variation | Relative activity (%) |
|---|---|---|
| KO (WILD) | | 100 |
| T124WN97Y | | 624 |
| T124WN97Y | E33A | 797 |
| T124WN97Y | E33S | 788 |

TABLE 8-continued

| Variation site | Additional variation | Relative activity (%) |
|---|---|---|
| T124WN97Y | E33W | 828 |
| T124WN97Y | E33G | 779 |
| T124WN97Y | E33F | 889 |
| T124WN97Y | E33Y | 810 |
| T124WN97Y | I80W | 876 |
| T124WN97Y | I80Y | 736 |
| T124WN97Y | I80R | 951 |
| T124WN97Y | I80F | 211 |
| T124WN97Y | I80C | 205 |
| T124WN97Y | I80T | 246 |
| T124WN97Y | I80S | 864 |
| T124WN97Y | I80L | 876 |
| T124WN97Y | I80K | 857 |
| T124WN97Y | I80E | 867 |
| T124WN97Y | Q102T | 198 |
| T124WN97Y | Q102A | 572 |
| T124WN97Y | Q102S | 698 |
| T124WN97Y | Q102P | 638 |
| T124WN97Y | Q102W | 620 |
| T124WN97Y | Q102L | 733 |
| T124WN97Y | Q102I | 803 |
| T124WN97Y | D137C | 745 |
| T124WN97Y | D137E | 618 |
| T124WN97Y | D137G | 555 |
| T124WN97Y | D137R | 551 |
| T124WN97Y | D137F | 580 |
| T124WN97Y | T210D | 347 |
| T124WN97Y | T210S | 421 |
| T124WN97Y | T210K | 370 |
| T124WN97Y | T210L | 417 |
| T124WN97Y | T210V | 806 |
| T124WN97Y | T210G | 870 |
| T124WN97Y | P318H | 337 |
| T124WN97Y | P318G | 635 |
| T124WN97Y | P318I | 479 |
| T124WN97Y | P318A | 571 |
| T124WN97Y | P318C | 854 |

TABLE 9

| Variation site | Additional variation | Relative activity (%) |
|---|---|---|
| KO (WILD) | | 100 |
| T124WN97YN367V | | 260.4 |
| T124WN97YN367V | E33W | 305.2 |
| T124WN97YN367V | I80R | 312.8 |
| T124WN97YN367V | Q102L | 418.4 |
| T124WN97YN367V | D137C | 335.2 |
| T124WN97YN367V | T210S | 373.2 |
| T124WN97YN367V | P318G | 322.0 |
| T124WN97YN367VE33W | I80R | 267.6 |
| T124WN97YN367VE33W | Q102L | 269.8 |
| T124WN97YN367VE33W | T210S | 271.3 |
| T124WN97YN367VE33W | P318G | 274.5 |
| T124WN97YN367VI80R | Q102L | 272.7 |
| T124WN97YN367VI80R | D137C | 266.5 |
| T124WN97YN367VI80R | T210S | 260.3 |
| T124WN97YN367VT210S | P318G | 269.5 |

These results indicate that the variants of the present disclosure have increased fructose-4-epimerization activity, as compared with the wild-type.

Example 5-2. Comparative Evaluation of Activity According to Number of Variations To compare the increase in the conversion rate according to the number of variations from the results of measuring the fructose-4-epimerization activity of the recombinant variant enzymes obtained in Example 5-1, 50 mM Tris-HCl (pH 8.0), 3 mM $MnSO_4$, and each 2 mg/mL of the enzymes were added to 30% by weight of fructose, and allowed to react at 50° C. or 60° C. for 2 hours.

As a result, all the variants of the present disclosure have increased fructose-4-epimerization activity, as compared with the wild-type (FIG. 3).

Example 5-3. Comparative Evaluation of Thermal Stability

To measure thermal stability of the obtained recombinant variant enzymes, each of the enzymes purified at a concentration of 5 mg/mL was added and left at 60° C. for at least 19 hours and up to 90 hours, and then left on ice for 5 minutes. Each of the enzyme solutions sampled at each time point, 50 mM Tris-HCl (pH 8.0), and 3 mM $MnSO_4$ were added to 30% by weight of fructose, and an enzymatic reaction was allowed to measure the residual activity of the enzymes.

The results of examining thermal stability showed that the fructose-4-epimerase variants showed reduction in the residual activity at 60° C. over time, but the thermal stability was more excellent than that of the wild-type, as shown in FIG. 4.

The present inventors transformed into *E. coli* BL21 (DE3) strain to prepare transformants (transformed microorganisms) designated as *E. coli* BL21(DE3)/CJ_KO_F4E_M3(T124W) and *E. coli* BL21(DE3)/CJ_KO_F4E_M8(T124W+N97Y), respectively and deposited the transformants on Sep. 19, 2018 at the Korean Culture Center of Microorganisms (KCCM) which is an international Depositary Authority under the provisions of the Budapest Treaty with Accession. Nos. KCCM12322P (*E. coli* BL21(DE3)/CJ_KO_F4E_M3) and KCCM12327P (*E. coli* BL21(DE3)/CJ_KO_F4E_M8), respectively.

Based on the above description, it will be understood by those skilled in the art that the present disclosure may be implemented in a different specific form without changing the technical spirit or essential characteristics thereof. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds are therefore intended to be embraced by the claims.

The invention claimed is:

1. A fructose-4-epimerase variant comprising substitution of another amino acid for a threonine (T) residue at position 124 from the N-terminus of fructose-4-epimerase including an amino acid sequence of SEQ ID NO: 1, wherein the variant includes an amino acid sequence having at least 60% sequence identity to the amino acid sequence of SEQ ID NO: 1.

2. The fructose-4-epimerase variant of claim 1, wherein the another amino acid is a polar amino acid or a nonpolar amino acid, except threonine (T).

3. The fructose-4-epimerase variant of claim 1, wherein the variant has further substitution of another amino acid for an amino acid at position 390.

4. The fructose-4-epimerase variant of claim 3, wherein the substituted amino acid at position 390 is a nonpolar amino acid, an acidic amino acid, or a basic amino acid.

5. The fructose-4-epimerase variant of claim 1, wherein the variant has further substitution of another amino acid for an amino acid at position 97.

6. The fructose-4-epimerase variant of claim 5, wherein the another amino acid is tyrosine (Y).

7. The fructose-4-epimerase variant of claim 5, wherein the variant has further substitution of another amino acid for any one of amino acids at positions 33, 80, 102, 137, 210, and 318.

8. The fructose-4-epimerase variant of claim 7, wherein the another amino acid is selected from the group consisting of a polar amino acid, a nonpolar amino acid, an acidic amino acid, and a basic amino acid.

9. The fructose-4-epimerase variant of claim 1, wherein the variant has further substitution of another amino acid for an amino acid at position 97 and substitution of another amino acid for an amino acid at position 367.

10. The fructose-4-epimerase variant of claim 9, wherein the another amino acid at position 97 is tyrosine (Y) and another amino acid at position 367 is valine (V).

11. The fructose-4-epimerase variant of claim 9, wherein the variant has further substitution of another amino acid for any one of amino acids at positions 102, 137, 210, 239, and 318.

12. The fructose-4-epimerase variant of claim 11, wherein the another amino acid is selected from the group consisting of a nonpolar amino acid, a polar amino acid, and a basic amino acid.

13. The fructose-4-epimerase variant of claim 9, wherein the variant has further substitution of another amino acid for an amino acid at position 33.

14. The fructose-4-epimerase variant of claim 13, wherein the another amino acid is arginine (R).

15. The fructose-4-epimerase variant of claim 13, wherein the variant has further substitution of another amino acid for any one of amino acids at positions 80, 102, 210, and 318.

16. The fructose-4-epimerase variant of claim 15, wherein the another amino acid is selected from the group consisting of a basic amino acid, a nonpolar amino acid, and a polar amino acid.

17. The fructose-4-epimerase variant of claim 9, wherein the variant has further substitution of another amino acid for an amino acid at position 80.

18. The fructose-4-epimerase variant of claim 17, wherein the another amino acid is arginine (R).

19. The fructose-4-epimerase variant of claim 17, wherein the variant has further substitution of another amino acid for any one of amino acids at positions 102, 137, and 210.

20. The fructose-4-epimerase variant of claim 19, wherein the another amino acid is a nonpolar amino acid or a polar amino acid.

21. The fructose-4-epimerase variant of claim 9, wherein the variant has further substitution of another amino acid for an amino acid at position 210 and substitution of another amino acid for an amino acid at position 318.

22. The fructose-4-epimerase variant of claim 21, wherein the another amino acid at position 210 is serine (S) and another amino acid at position 318 is glycine (G).

23. A polynucleotide encoding the fructose-4-epimerase variant of claim 1.

24. A vector comprising the polynucleotide of claim 23.

25. A microorganism comprising the fructose-4-epimerase variant of claim 1; a polynucleotide encoding the fructose-4-epimerase variant; or a vector including the polynucleotide.

26. A composition for producing tagatose, the composition comprising the fructose-4-epimerase variant of claim 1; a microorganism expressing the fructose-4-epimerase variant; or a culture of the microorganism.

27. The composition for producing tagatose of claim 26, the composition further comprising fructose.

28. A method of producing tagatose, the method comprising the step of converting fructose into tagatose by contacting fructose with the fructose-4-epimerase variant of claim 1; the microorganism including the fructose-4-epimerase variant; or the culture thereof.

* * * * *

SEQUENCE LISTING

<160> NUMBER OF SEQ ID NOS: 26

<210> SEQ ID NO 1
<211> LENGTH: 435
<212> TYPE: PRT
<213> ORGANISM: Unknown
<220> FEATURE:

<223> OTHER INFORMATION: Kosmotoga olearia
<220> FEATURE:
<221> NAME/KEY: PEPTIDE
<222> LOCATION: (1)..(435)
<223> OTHER INFORMATION: Tagatose-bisphosphate aldolase

<400> SEQUENCE: 1

```
Met Lys Lys His Pro Leu Gln Asp Ile Val Ser Leu Gln Lys Gln Gly
 1               5                  10                  15

Ile Pro Lys Gly Val Phe Ser Val Cys Ser Ala Asn Arg Phe Val Ile
                20                  25                  30

Glu Thr Thr Leu Glu Tyr Ala Lys Met Lys Gly Thr Thr Val Leu Ile
            35                  40                  45

Glu Ala Thr Cys Asn Gln Val Asn Gln Phe Gly Gly Tyr Thr Gly Met
        50                  55                  60

Thr Pro Ala Asp Phe Arg Glu Met Val Phe Ser Ile Ala Glu Asp Ile
65                  70                  75                  80

Gly Leu Pro Lys Asn Lys Ile Ile Leu Gly Gly Asp His Leu Gly Pro
                85                  90                  95

Asn Pro Trp Lys Gly Gln Pro Ser Asp Gln Ala Met Arg Asn Ala Ile
            100                 105                 110

Glu Met Ile Arg Glu Tyr Ala Lys Ala Gly Phe Thr Lys Leu His Leu
        115                 120                 125

Asp Ala Ser Met Arg Leu Ala Asp Asp Pro Gly Asn Glu Asn Glu Pro
130                 135                 140

Leu Asn Pro Glu Val Ile Ala Glu Arg Thr Ala Leu Leu Cys Leu Glu
145                 150                 155                 160

Ala Glu Arg Ala Phe Lys Glu Ser Ala Gly Ser Leu Arg Pro Val Tyr
                165                 170                 175

Val Ile Gly Thr Asp Val Pro Pro Gly Gly Ala Gln Asn Glu Gly
            180                 185                 190

Lys Ser Ile His Val Thr Ser Val Gln Asp Phe Glu Arg Thr Val Glu
        195                 200                 205

Leu Thr Lys Lys Ala Phe Phe Asp His Gly Leu Tyr Glu Ala Trp Gly
210                 215                 220

Arg Val Ile Ala Val Val Val Gln Pro Gly Val Glu Phe Gly Asn Glu
225                 230                 235                 240

His Ile Phe Glu Tyr Asp Arg Asn Arg Ala Arg Glu Leu Thr Glu Ala
                245                 250                 255

Ile Lys Lys His Pro Asn Ile Val Phe Glu Gly His Ser Thr Asp Tyr
            260                 265                 270

Gln Thr Ala Lys Ala Leu Lys Glu Met Val Glu Asp Gly Val Ala Ile
        275                 280                 285

Leu Lys Val Gly Pro Ala Leu Thr Phe Ala Leu Arg Glu Ala Phe Phe
290                 295                 300

Ala Leu Ser Ser Ile Glu Lys Glu Leu Phe Tyr Asp Thr Pro Gly Leu
305                 310                 315                 320

Cys Ser Asn Phe Val Glu Val Val Arg Ala Met Leu Asp Asn Pro
                325                 330                 335

Lys His Trp Glu Lys Tyr Tyr Gln Gly Glu Arg Glu Asn Arg Leu
            340                 345                 350

Ala Arg Lys Tyr Ser Phe Leu Asp Arg Leu Tyr Tyr Trp Asn Leu
        355                 360                 365

Pro Glu Val Arg Thr Ala Val Asn Lys Leu Ile Thr Asn Leu Glu Thr
370                 375                 380
```

```
Lys Glu Ile Pro Leu Thr Leu Ile Ser Gln Phe Met Pro Met Gln Tyr
385                 390                 395                 400

Gln Lys Ile Arg Asn Gly Leu Leu Arg Lys Asp Pro Ile Ser Leu Ile
            405                 410                 415

Lys Asp Arg Ile Thr Leu Val Leu Asp Asp Tyr Tyr Phe Ala Thr His
        420                 425                 430

Pro Glu Cys
        435

<210> SEQ ID NO 2
<211> LENGTH: 1308
<212> TYPE: DNA
<213> ORGANISM: Unknown
<220> FEATURE:
<223> OTHER INFORMATION: Kosmotoga olearia
<220> FEATURE:
<221> NAME/KEY: gene
<222> LOCATION: (1)..(1308)
<223> OTHER INFORMATION: Tagatose-bisphosphate aldolase

<400> SEQUENCE: 2
atgaaaaaac atcctcttca ggacattgtt tcattgcaaa acagggaat acccaaaggg      60 gttttctctg tatgtagtgc aatagatttt gttattgaaa ccactctgga atatgcgaag    120
atgaaaggga caacggttct tatagaggcc acctgcaatc aggtaaacca gttcggtggc    180
tacaccggta tgactcctgc tgatttcaga gaaatggttt tttctatcgc tgaggatatt    240
ggacttccca aaaataaaat catccttggt ggcgaccatc ttggcccaaa tccctggaag    300
ggtcagccgt cagatcaggc tatgcgtaac gccattgaaa tgattcgaga atacgctaaa    360
gctgggttta ccaagcttca tctggatgcc agcatgcgtc ttgcagacga tccggggaac    420
gaaaacgagc cgctgaaccc ggaagttata gcggaaagaa cagctcttct ctgtcttgaa    480
gccgagaggg cttttaaaga atccgccggt tctctccggc ctgtttacgt tattggtacg    540
gatgttccgc caccgggtgg agcgcaaaac gaaggtaaat cgattcatgt aaccagtgtt    600
caggattttg agcgtaccgt tgagttgacc aaaaaggcat ttttcgacca tggtttgtat    660
gaagcctggg aagggtgat gcggttgtt gtgcaaccgg gagtagaatt cgggaatgaa     720
catatattcg aatatgatag aaatcgagcg agagaactta ctgaggcgat aaaaaagcat    780
ccaaatatag ttttttgaagg tcactcgaca gattatcaaa cggcaaaagc attgaaagaa    840
atggtagaag acggtgtagc catactcaag gttgggccag ctctaacatt gcgctcaga    900 gaggcttttt ttgcgttgag cagcattgaa aaagagttat tttatgatac acccgggctt    960
tgttcaaact tgttgaagt tgtcgagaga gcgatgcttg acaatccaaa acattgggaa   1020
aaatattacc aggagaaga gagagaaaat agattagccc gtaaatacag ctttctcgat   1080
cgcttgaggt attactggaa tcttcctgag gttagaacag cggtgaataa gctgataacc   1140
aaccttgaaa caaagaaat cccgttaacg cttataagcc agttcatgcc gatgcagtac   1200
caaaaaatca gaacggttt gctaagaaag gatccaataa gccttataaa agatcgaatt   1260
acccttgttc ttgatgacta ctatttcgca actcaccctg aatgttga                1308

<210> SEQ ID NO 3
<211> LENGTH: 434
<212> TYPE: PRT
<213> ORGANISM: Unknown
<220> FEATURE:
<223> OTHER INFORMATION: Thermoanaerobacterium thermosaccharolyticum
<220> FEATURE:
```

<221> NAME/KEY: PEPTIDE
<222> LOCATION: (1)..(434)
<223> OTHER INFORMATION: Tagatose-bisphosphate aldolase

<400> SEQUENCE: 3

Met Ala Lys Glu His Pro Leu Lys Glu Leu Val Asn Lys Gln Lys Ser
1               5                   10                  15

Gly Ile Ser Glu Gly Ile Val Ser Ile Cys Ser Ser Asn Glu Phe Val
            20                  25                  30

Ile Glu Ala Ser Met Glu Arg Ala Leu Thr Asn Gly Asp Tyr Val Leu
        35                  40                  45

Ile Glu Ser Thr Ala Asn Gln Val Asn Gln Tyr Gly Gly Tyr Ile Gly
    50                  55                  60

Met Thr Pro Ile Glu Phe Lys Lys Phe Val Phe Ser Ile Ala Lys Lys
65                  70                  75                  80

Val Asp Phe Pro Leu Asp Lys Leu Ile Leu Gly Gly Asp His Leu Gly
                85                  90                  95

Pro Leu Ile Trp Lys Asn Glu Ser Ser Asn Leu Ala Leu Ala Lys Ala
            100                 105                 110

Ser Glu Leu Ile Lys Glu Tyr Val Leu Ala Gly Tyr Thr Lys Ile His
        115                 120                 125

Ile Asp Thr Ser Met Arg Leu Lys Asp Thr Asp Phe Asn Thr Glu
    130                 135                 140

Ile Ile Ala Gln Arg Ser Ala Val Leu Leu Lys Ala Ala Glu Asn Ala
145                 150                 155                 160

Tyr Met Glu Leu Asn Lys Asn Lys Asn Val Leu His Pro Val Tyr
                165                 170                 175

Val Ile Gly Ser Glu Val Pro Ile Pro Gly Gly Ser Gln Gly Ser Asp
            180                 185                 190

Glu Ser Leu Gln Ile Thr Asp Ala Lys Asp Phe Glu Asn Thr Val Glu
        195                 200                 205

Ile Phe Lys Asp Val Phe Ser Lys Tyr Gly Leu Ile Asn Glu Trp Glu
    210                 215                 220

Asn Ile Val Ala Phe Val Val Gln Pro Gly Val Glu Phe Gly Asn Asp
225                 230                 235                 240

Phe Val His Glu Tyr Lys Arg Asp Glu Ala Lys Glu Leu Thr Asp Ala
                245                 250                 255

Leu Lys Asn Tyr Lys Thr Phe Val Phe Glu Gly His Ser Thr Asp Tyr
            260                 265                 270

Gln Thr Arg Glu Ser Leu Lys Gln Met Val Glu Asp Gly Ile Ala Ile
        275                 280                 285

Leu Lys Val Gly Pro Ala Leu Thr Phe Ala Leu Arg Glu Ala Leu Ile
    290                 295                 300

Ala Leu Asn Asn Ile Glu Asn Glu Leu Leu Asn Asn Val Asp Ser Ile
305                 310                 315                 320

Lys Leu Ser Asn Phe Thr Asn Val Leu Val Ser Glu Met Ile Asn Asn
                325                 330                 335

Pro Glu His Trp Lys Asn His Tyr Phe Gly Asp Asp Ala Arg Lys Lys
            340                 345                 350

Phe Leu Cys Lys Tyr Ser Tyr Ser Asp Arg Cys Arg Tyr Tyr Leu Pro
        355                 360                 365

Thr Arg Asn Val Lys Asn Ser Leu Asn Leu Ile Arg Asn Leu Glu
    370                 375                 380

Asn Val Lys Ile Pro Met Thr Leu Ile Ser Gln Phe Met Pro Leu Gln

```
                385                 390                 395                 400
Tyr Asp Asn Ile Arg Arg Gly Leu Ile Lys Asn Glu Pro Ile Ser Leu
                    405                 410                 415

Ile Lys Asn Ala Ile Met Asn Arg Leu Asn Asp Tyr Tyr Tyr Ala Ile
                420                 425                 430

Lys Pro

<210> SEQ ID NO 4
<211> LENGTH: 1305
<212> TYPE: DNA
<213> ORGANISM: Unknown
<220> FEATURE:
<223> OTHER INFORMATION: Thermoanaerobacterium thermosaccharolyticum
<220> FEATURE:
<221> NAME/KEY: gene
<222> LOCATION: (1)..(1305)
<223> OTHER INFORMATION: Tagatose-bisphosphate aldolase

<400> SEQUENCE: 4
atggctaaag aacatccatt aaaggaatta gtaaataaac aaaaaagtgg tatatccgag      60
ggtatagttt ctatttgtag ttcaaatgaa tttgttattg aagcatctat ggagcgtgca     120
ttaacaaatg gtgattatgt tttaattgaa tcaacagcaa tcaggtgaa tcaatatggt     180 ggatatattg gtatgacacc tattgagttt aaaaaatttg tattttcaat agctaaaaaa     240
gtagattttc cattagataa attgattctt ggtggggatc atttagggcc attaatatgg     300
aaaaatgaat ctagtaattt ggcgttagca aaagcatccg agcttattaa agaatatgta     360
ttagccggat atactaaaat tcatatagac actagtatgc ggctaaaaga tgatactgat     420
tttaatacag aaattattgc tcaaagaagt gcagtattgt taaaggcagc ggaaaatgca     480
tatatggaat tgaataaaaa taataaaaat gttttacatc ctgtctatgt tataggaagt     540
gaagtcccaa tacctggggg cagccaaggc agtgatgaat cgctccaaat tactgatgct     600
aaggattttg aaaatacagt tgaaatattt aaagatgttt tttcaaaata tggattaatt     660
aatgagtggg aaaacatagt agcatttgtt gttcaaccag gagttgagtt tggaaatgat     720
tttgtacatg aatataaacg tgatgaagca aaagaattaa cagatgcact taaaaattat     780
aaaacatttg ttttttgaagg acattctact gattatcaaa cacgtgaatc attaaaacaa     840
atggtggaag atggcattgc aattttaaaa gttggacctg cattaacatt tgcactacgt     900
gaagccttaa tagcactaaa taatatagaa atgagttgc ttaataatgt agatagtata     960
aaattatcaa attttactaa tgtactcgta agtgaaatga tcaataaccc cgaacattgg    1020
aaaaatcatt attttggtga tgatgcaagg aaaaagtttc tatgtaaata tagttattcg    1080
gatagatgta ggtactattt accaactaga aatgtaaaaa actcattaaa tcttcttatt    1140
agaaatctag aaaatgtgaa ataccaatg acattaataa gtcaatttat gcctttgcaa    1200
tatgataata ttagaagagg actcataaaa aatgaaccaa tttctttaat taaaaatgca    1260
ataatgaacc gacttaatga ctattattat gctataaagc cgtaa                   1305

<210> SEQ ID NO 5
<211> LENGTH: 434
<212> TYPE: PRT
<213> ORGANISM: Unknown
<220> FEATURE:
<223> OTHER INFORMATION: Pseudoalteromonas sp. H103
<220> FEATURE:
<221> NAME/KEY: PEPTIDE
<222> LOCATION: (1)..(434)
<223> OTHER INFORMATION: Tagatose-bisphosphate aldolase
```

<400> SEQUENCE: 5

```
Met Arg Gly Asp Lys Arg Val Thr Thr Asp Phe Leu Lys Glu Ile Val
1               5                   10                  15

Gln Gln Asn Arg Ala Gly Gly Ser Arg Gly Ile Tyr Ser Val Cys Ser
            20                  25                  30

Ala His Arg Leu Val Ile Glu Ala Ser Met Gln Gln Ala Lys Ser Asp
        35                  40                  45

Gly Ser Pro Leu Leu Val Glu Ala Thr Cys Asn Gln Val Asn His Glu
    50                  55                  60

Gly Gly Tyr Thr Gly Met Thr Pro Ser Asp Phe Cys Lys Tyr Val Leu
65                  70                  75                  80

Asp Ile Ala Lys Glu Val Gly Phe Ser Gln Glu Gln Leu Ile Leu Gly
                85                  90                  95

Gly Asp His Leu Gly Pro Asn Pro Trp Thr Asp Leu Pro Ala Ala Gln
            100                 105                 110

Ala Met Glu Ala Ala Lys Lys Met Val Ala Asp Tyr Val Ser Ala Gly
        115                 120                 125

Phe Ser Lys Ile His Leu Asp Ala Ser Met Ala Cys Ala Asp Asp Val
130                 135                 140

Glu Pro Leu Ala Asp Glu Val Ile Ala Gln Arg Ala Thr Ile Leu Cys
145                 150                 155                 160

Ala Ala Gly Glu Ala Ala Val Ser Asp Lys Asn Ala Ala Pro Met Tyr
                165                 170                 175

Ile Ile Gly Thr Glu Val Pro Val Pro Gly Gly Ala Gln Glu Asp Leu
            180                 185                 190

His Glu Leu Ala Thr Thr Asn Ile Asp Asp Leu Lys Gln Thr Ile Lys
        195                 200                 205

Thr His Lys Ala Lys Phe Ser Glu Asn Gly Leu Gln Asp Ala Trp Asp
210                 215                 220

Arg Val Ile Gly Val Val Gln Pro Gly Val Glu Phe Asp His Ala
225                 230                 235                 240

Met Val Ile Gly Tyr Gln Ser Glu Lys Ala Gln Thr Leu Ser Lys Thr
                245                 250                 255

Ile Leu Asp Phe Asp Asn Leu Val Tyr Glu Ala His Ser Thr Asp Tyr
            260                 265                 270

Gln Thr Glu Thr Ala Leu Thr Asn Leu Val Asn Asp His Phe Ala Ile
        275                 280                 285

Leu Lys Val Gly Pro Gly Leu Thr Tyr Ala Ala Arg Glu Ala Leu Phe
290                 295                 300

Ala Leu Ser Tyr Ile Glu Gln Glu Trp Ile Thr Asn Lys Pro Leu Ser
305                 310                 315                 320

Asn Leu Arg Gln Val Leu Glu Glu Arg Met Leu Glu Asn Pro Lys Asn
                325                 330                 335

Trp Ala Lys Tyr Tyr Thr Gly Thr Glu Gln Gln Ala Phe Ala Arg
            340                 345                 350

Lys Tyr Ser Phe Ser Asp Arg Ser Arg Tyr Tyr Trp Ala Asp Pro Ile
        355                 360                 365

Val Asp Gln Ser Val Gln Thr Leu Ile Asn Asn Leu Thr Glu Gln Pro
370                 375                 380

Ala Pro Met Thr Leu Leu Ser Gln Phe Met Pro Leu Gln Tyr Ala Ala
385                 390                 395                 400

Phe Arg Ala Gly Gln Leu Asn Asn Asp Pro Leu Ser Leu Ile Arg His
```

405                 410                 415
Trp Ile Gln Glu Val Val Ser Thr Tyr Ala Arg Ala Ser Gly Leu Ala
                420                 425                 430

Val Lys

<210> SEQ ID NO 6
<211> LENGTH: 1305
<212> TYPE: DNA
<213> ORGANISM: Unknown
<220> FEATURE:
<223> OTHER INFORMATION: Pseudoalteromonas sp. H103
<220> FEATURE:
<221> NAME/KEY: gene
<222> LOCATION: (1)..(1305)
<223> OTHER INFORMATION: Tagatose-bisphosphate aldolase

<400> SEQUENCE: 6

```
atcagaggag ataaaagggt gactacagat tttctgaaag aaattgttca acaaaacaga      60
gccggtggta gcagaggtat ttactctgtt tgttctgcgc atcgccttgt tattgaagcg     120
tctatgcagc aagccaaaag cgatggctca ccactgttag tagaggcaac atgtaatcag     180
gttaatcacg aaggtggtta taccggtatg accccaagcg acttttgcaa atacgtgtta     240
gatattgcaa aagaagtggg cttttcccaa gagcaactta ttttaggggg cgaccactta     300
gggcctaacc cgtggactga cctaccagct gcacaggcaa tggaagcggc caaaaaaatg     360
gttgctgatt acgtaagtgc gggcttttca aaaatacatt tagatgcaag catggcatgt     420
gcagatgatg tagagccgct tgctgatgag gttatagcgc agcgcgccac tattttatgt     480
gctgccggcg aagctgctgt tagcgataaa aatgcagccc aatgtatat  tattggtacc     540
gaagtgccgg taccaggtgg cgcacaagaa gatttacacg aacttgctac aaccaatatt     600
gatgatttaa acaaaccat  taaaacccat aaagcaaaat ttagcgaaaa cggtttgcaa     660
gacgcatggg atagagtaat tggtgtagta gtgcagcctg tgttgagtt  tgaccacgcg     720
atggtaattg gctatcaaag cgaaaaagca caaacactaa gtaaaactat tttagatttt     780
gataatttgg tttatgaagc gcattcaacc gattatcaaa ccgaaacagc gttaactaac     840
ttggttaacg accactttgc tattttaaaa gtgggcccag gcttactta  tgcagcgcgc     900
gaagcgttgt ttgcacttag ttatattgag caagagtgga taaccaataa gcctctttct     960
aatttgcgcc aagtgcttga agagcgcatg ctcgaaaacc ctaaaaactg gctaagtat    1020
tacacaggta cagagcaaga gcaggccttt gcacgaaaat atagctttag cgatagatcg    1080
cgttactatt gggccgatcc tattgttgat caaagtgttc aaacactcat taataactta    1140
actgagcagc cagcgccaat gaccttgctg agtcaattta tgccacttca atatgcggca    1200
tttcgtgcag acaattaaa  taacgatccg ctttctttga tcagacactg gatccaagaa    1260
gttgtatcaa cctacgcccg cgctagcgga cttgcagtaa aatag                    1305
```

<210> SEQ ID NO 7
<211> LENGTH: 426
<212> TYPE: PRT
<213> ORGANISM: Unknown
<220> FEATURE:
<223> OTHER INFORMATION: Thermanaerothrix daxensis
<220> FEATURE:
<221> NAME/KEY: PEPTIDE
<222> LOCATION: (1)..(426)
<223> OTHER INFORMATION: Tagatose-biphosphate aldolase

<400> SEQUENCE: 7

```
Met Val Thr Tyr Leu Asp Phe Val Val Leu Ser His Arg Phe Arg Arg
1               5                   10                  15

Pro Leu Gly Ile Thr Ser Val Cys Ser Ala His Pro Tyr Val Ile Glu
            20                  25                  30

Ala Ala Leu Arg Asn Gly Met Met Thr His Thr Pro Val Leu Ile Glu
            35                  40                  45

Ala Thr Cys Asn Gln Val Asn Gln Tyr Gly Gly Tyr Thr Gly Met Thr
        50                  55                  60

Pro Ala Asp Phe Val Arg Tyr Val Glu Asn Ile Ala Ala Arg Val Gly
65                  70                  75                  80

Ser Pro Arg Glu Asn Leu Leu Gly Gly Asp His Leu Gly Pro Leu
                85                  90                  95

Val Trp Ala His Glu Pro Ala Glu Ser Ala Met Glu Lys Ala Arg Ala
                100                 105                 110

Leu Val Lys Ala Tyr Val Glu Ala Gly Phe Arg Lys Ile His Leu Asp
            115                 120                 125

Cys Ser Met Pro Cys Ala Asp Asp Arg Asp Phe Ser Pro Lys Val Ile
        130                 135                 140

Ala Glu Arg Ala Ala Glu Leu Ala Gln Val Ala Glu Ser Thr Cys Asp
145                 150                 155                 160

Val Met Gly Leu Pro Leu Pro Asn Tyr Val Ile Gly Thr Glu Val Pro
                165                 170                 175

Pro Ala Gly Gly Ala Lys Ala Glu Ala Glu Thr Leu Arg Val Thr Arg
            180                 185                 190

Pro Glu Asp Ala Ala Glu Thr Ile Ala Leu Thr Arg Ala Ala Phe Phe
        195                 200                 205

Lys Arg Gly Leu Glu Ser Ala Trp Glu Arg Val Val Ala Leu Val Val
210                 215                 220

Gln Pro Gly Val Glu Phe Gly Asp His Gln Ile His Val Tyr Arg Arg
225                 230                 235                 240

Glu Glu Ala Gln Ala Leu Ser Arg Phe Ile Glu Ser Gln Pro Gly Leu
                245                 250                 255

Val Tyr Glu Ala His Ser Thr Asp Tyr Gln Pro Arg Asp Ala Leu Arg
                260                 265                 270

Ala Leu Val Glu Asp His Phe Ala Ile Leu Lys Val Gly Pro Ala Leu
            275                 280                 285

Thr Phe Ala Phe Arg Glu Ala Val Phe Ala Leu Ala Ser Ile Glu Asp
        290                 295                 300

Trp Val Cys Asp Ser Pro Ser Arg Ile Leu Glu Val Leu Glu Thr Thr
305                 310                 315                 320

Met Leu Ala Asn Pro Val Tyr Trp Gln Lys Tyr Tyr Leu Gly Asp Glu
                325                 330                 335

Arg Ala Arg Arg Ile Ala Arg Gly Tyr Ser Phe Ser Asp Arg Ile Arg
            340                 345                 350

Tyr Tyr Trp Ser Ala Pro Ala Val Glu Gln Ala Phe Glu Arg Leu Arg
        355                 360                 365

Ala Asn Leu Asn Arg Val Ser Ile Pro Leu Val Leu Leu Ser Gln Tyr
370                 375                 380

Leu Pro Asp Gln Tyr Arg Lys Val Arg Asp Gly Arg Leu Pro Asn Gln
385                 390                 395                 400

Phe Asp Ala Leu Ile Leu Asp Lys Ile Gln Ala Val Leu Glu Asp Tyr
                405                 410                 415

Asn Val Ala Cys Gly Val Arg Ile Gly Glu
```

420        425

<210> SEQ ID NO 8
<211> LENGTH: 1281
<212> TYPE: DNA
<213> ORGANISM: Unknown
<220> FEATURE:
<223> OTHER INFORMATION: Thermanaerothrix daxensis
<220> FEATURE:
<221> NAME/KEY: gene
<222> LOCATION: (1)..(1281)
<223> OTHER INFORMATION: Tagatose-biphosphate aldolase

<400> SEQUENCE: 8

```
atggttacct atttggattt tgtggtgctt tctcatcgtt ttaggcgccc cctgggcatt      60
acctcagtgt gttcggcgca tccgtatgtc attgaggcgg cgctgcgtaa tgggatgatg     120
acccatacac cggtcctaat cgaggccact tgcaatcaag tcaatcagta tgggggatat     180
acggggatga ccccggcaga tttcgtgcgg tatgtggaga atattgctgc acgggtaggc     240
tctccacgtg aaaacctcct tttgggtggc gatcatttgg acccctggt ctgggctcat      300 gaacctgctg agagtgccat ggaaaaagct cgagctctgg tcaaagccta tgtagaggct     360
ggttttcgca aaattcatct ggattgctca atgccctgtg cggatgatcg cgattttct      420 ccaaaggtca ttgctgagcg ggcagccgaa ttggctcagg tggcagagtc aacttgtgat     480
gttatgggct tgcccttgcc caactacgtc attgaaccg aggtgccccc agcaggtggc      540
gccaaggctg aagccgaaac tttgagggta acccgtccgg aggatgcagc ggagaccatt     600
gcactgacca gagcggcttt tttcaagcga ggtttagagt ctgcctggga acgtgtagtg     660
gcgttagtag tgcaacccgg tgttgaattc ggagatcatc agattcatgt ttaccgccgt     720
gaggaagcgc aggctctttc ccgcttcatt gaaagccagc ccggcttagt ctatgaggct     780
cactccaccg actatcagcc ccgtgatgcg ctgcgggctt tggttgagga tcatttcgca     840
atcctgaagg tgggtccggc gctaaccttt gcttttcgtg aggcagtttt tgccctggcc     900
agtatcgagg attgggtatg cgattcaccc agtcgcatcc tggaagtttt ggaaacaacc     960
atgctggcca acccggtcta ctggcaaaag tattacttgg gcgatgagcg agcgcgtcgg    1020
attgccagag ggtatagttt cagcgatcgc attcgttatt attggagtgc accagcggtt    1080
gaacaggcct tgaacgcttc gcgggcaaat ctgaatcgtg tttcgatccc ccttgtcctt    1140
ctcagtcagt atttgccgga tcaatatcgc aaagtgcggg atggacggct gcctaaccag    1200
tttgatgctt tgattctgga taaaatccaa gccgtactgg aagactacaa tgtggcgtgt    1260
ggtgtgagga tagggagtg a                                                1281
```

<210> SEQ ID NO 9
<211> LENGTH: 431
<212> TYPE: PRT
<213> ORGANISM: Unknown
<220> FEATURE:
<223> OTHER INFORMATION: Acidobacteriales bacterium
<220> FEATURE:
<221> NAME/KEY: PEPTIDE
<222> LOCATION: (1)..(431)
<223> OTHER INFORMATION: Tagatose-biphosphate aldolase

<400> SEQUENCE: 9

Met Ser Asp Asn Leu Gln Val Phe Leu Arg Glu Ser Arg Gly Arg Arg
1               5                   10                  15

Gly Ile Tyr Ser Val Cys Ser Ala His Pro Arg Val Ile Glu Ala Ala
            20                  25                  30

-continued

```
Met Arg Gln Ala Gly Ala Asp Gly Thr His Leu Leu Glu Ala Thr
         35                  40                  45

Ser Asn Gln Val Asn Gln Ala Gly Gly Tyr Thr Gly Met Thr Pro Ala
     50                  55                  60

Met Phe Arg Asp Tyr Val Tyr Asp Ile Ala Gln Glu Ile Gly Phe Asp
 65                  70                  75                  80

Arg Ser Arg Leu Ile Leu Gly Gly Asp His Leu Gly Pro Asn Pro Trp
                     85                  90                  95

Gln Gln Leu Asp Ala Ser Thr Ala Met Gln Tyr Ala Glu Glu Met Val
                100                 105                 110

Arg Leu Tyr Ile Glu Ala Gly Phe Thr Lys Ile His Leu Asp Ala Ser
            115                 120                 125

Met Arg Cys Ala Asp Asp Ala Ile Val Pro Asp Glu Val Met Ala
        130                 135                 140

Gly Arg Ala Ala Leu Cys Ser Ala Ala Glu Ser Ala Arg Ala Arg
145                 150                 155                 160

Leu Gly Leu Ala Pro Val Val Tyr Val Ile Gly Thr Glu Val Pro Thr
                    165                 170                 175

Pro Gly Gly Ala Ser His Ala Leu Asn Thr Leu Glu Val Thr Thr Arg
                180                 185                 190

Glu Ala Val Glu His Thr Leu Ser Val His Arg Lys Ala Phe His Asp
            195                 200                 205

Ala Gly Leu Asp Ala Ala Trp Gln Arg Val Ile Ala Val Val Gln
        210                 215                 220

Pro Gly Val Glu Phe Asp His Asp Ser Val Val Asp Tyr Asp Ala Ala
225                 230                 235                 240

Lys Ala Gly His Leu Gln Glu Phe Leu Gln Ala His Pro Glu Leu Val
                    245                 250                 255

Met Glu Ala His Ser Ser Asp Tyr Gln Lys Pro Gln Ala Tyr Lys Glu
                260                 265                 270

Leu Val Arg Asp Gly Phe Ala Ile Leu Lys Val Gly Pro Ala Leu Thr
            275                 280                 285

Phe Ala Leu Arg Glu Met Leu Tyr Ala Leu Ala Ala Ile Glu Arg Glu
        290                 295                 300

Leu Val Pro Glu Ala Glu Gln Ser His Leu Val Glu Thr Met Glu Glu
305                 310                 315                 320

Ile Met Leu Ala His Pro Glu Asn Trp Gln Lys Tyr Tyr Arg Gly Ser
                    325                 330                 335

Ala Glu Gln Gln Arg Leu Leu Arg Val Tyr Ser Tyr Ser Asp Arg Ile
                340                 345                 350

Arg Tyr Tyr Trp Gly Arg Pro Glu Ala Glu Ala Val Thr Arg Leu
            355                 360                 365

Met Arg Asn Leu His Gln Thr Thr Ile Pro Glu Thr Leu Leu Ser Gln
        370                 375                 380

Tyr Cys Pro Arg Glu Tyr Gly Ala Met Arg Glu Gly Arg Leu Arg Asn
385                 390                 395                 400

Asp Pro Ala Glu Leu Thr Ile Ala Ser Ile Arg Thr Val Leu Glu Ser
                    405                 410                 415

Tyr Ser Ser Ala Cys Arg Gly Asp Gly Ser Asn Ser Gly Lys Gln
                420                 425                 430

<210> SEQ ID NO 10
<211> LENGTH: 1296
```

```
<212> TYPE: DNA
<213> ORGANISM: Unknown
<220> FEATURE:
<223> OTHER INFORMATION: Acidobacteriales bacterium
<220> FEATURE:
<221> NAME/KEY: gene
<222> LOCATION: (1)..(1296)
<223> OTHER INFORMATION: Tagatose-biphosphate aldolase

<400> SEQUENCE: 10
atgtccgaca atttgcaggt gtttcttcgt gagtcccgag gccggcgcgg catctattcg      60
gtatgctccg cgcatccccg ggtgatcgag gccgccatgc ggcaagctgg cgcagacggc     120
acgcatctgc tgctggaagc gacgtcgaat caggtgaacc aagccggagg ctacaccggc     180
atgactcccg cgatgtttcg cgattacgtt tatgacattg cacaggagat cggcttcgac     240
cgcagccgtt tgattcttgg cggagatcat ttgggcccca atccctggca gcagctcgac     300
gccagcacag cgatgcagta tgcagaggag atggttcgac tgtacatcga ggcaggattc     360
accaagattc atctcgacgc cagcatgcgt tgtgccgacg atgcggcaat cgttcccgat     420
gaagtgatgg caggacgcgc cgccgcattg tgcagcgcgg ctgagtcggc gcgagcacgg     480
ctgggactgg cgccggtggt ctacgtgatc ggaaccgagg ttccaacgcc gggtggagca     540
agccatgctc tcaacacgct ggaggtaaca acgcgggagg cagtcgagca tacgctgtcg     600
gttcatcgca agccttcca cgatgcggga ttggacgctg catggcagcg cgtgatcgcg     660
gtggtcgtgc agccgggcgt ggagttcgat cacgatagcg ttgtcgacta tgacgccgca     720
aaagcgggcc atttgcaaga atttctacaa gcccacccgg aactggtgat ggaggcacac     780
tccagcgatt accagaagcc gcaagcctac aaggaactgg tccgtgatgg cttcgcgatc     840
ctgaaggtcg ggcctgcgtt gacgtttgcg ctgcgggaga tgctctacgc gctggccgcc     900
atcgagcggg aactggtgcc ggaggcggag cagtcccatc tggtagagac gatggaagag     960
atcatgctgg ctcatcccga gaactggcag aagtactatc gcggaagcgc agagcagcag    1020
cgattgctgc gcgtctatag ctacagcgac cgcattcgct attactgggg acgtccggag    1080
gccgaagctg ccgtcacgcg cctgatgcga aatctgcatc agacgacgat tcccgagact    1140
ctcctaagcc agtattgtcc gcgcgaatat gaggcaatgc gcgaaggaag actgcgaaac    1200
gatccggctg agttgacgat cgcgagcatt cgaactgtgc tggagtccta cagcagcgct    1260
tgtcgcggtg acggctcgaa ctccggtaaa cagtaa                              1296

<210> SEQ ID NO 11
<211> LENGTH: 420
<212> TYPE: PRT
<213> ORGANISM: Unknown
<220> FEATURE:
<223> OTHER INFORMATION: Rhodothermus profundi
<220> FEATURE:
<221> NAME/KEY: PEPTIDE
<222> LOCATION: (1)..(420)
<223> OTHER INFORMATION: Tagatose-biphosphate aldolase

<400> SEQUENCE: 11

Met Gln Ala His Val Leu Leu Ala Pro Ser Phe Glu Gln Leu Ala Asp
1               5                   10                  15

His Arg His Gly Phe Val Gly Trp Leu Val Asp Leu Leu Arg Gly Pro
                20                  25                  30

Leu Ala Tyr Arg His Thr Leu Leu Ala Val Cys Pro Asn Ser Glu Ala
            35                  40                  45

Val Thr Arg Ala Ala Leu Glu Ala Ala Arg Glu Ala Asn Ala Pro Leu
```

Phe Phe Ala Ala Thr Leu Asn Gln Val Asp Leu Asp Gly Gly Tyr Thr
65                  70                  75                  80

Gly Trp Thr Pro Ala Thr Leu Ala Arg Phe Val Ala Asp Glu Arg Ile
                85                  90                  95

Arg Leu Gly Leu Arg Ala Pro Val Val Leu Gly Leu Asp His Gly Gly
            100                 105                 110

Pro Trp Lys Lys Asp Trp His Val Arg Asn Arg Leu Pro Tyr Glu Ala
            115                 120                 125

Thr Leu Gln Ala Val Leu Arg Ala Ile Glu Ala Cys Leu Asp Ala Gly
130                 135                 140

Tyr Gly Leu Leu His Leu Asp Pro Thr Val Asp Leu Glu Leu Pro Pro
145                 150                 155                 160

Gly Thr Pro Val Pro Ile Pro Arg Ile Val Glu Arg Thr Val Ala Leu
                165                 170                 175

Leu Gln His Ala Glu Thr Tyr Arg Gln Arg Arg Leu Pro Pro Val
            180                 185                 190

Ala Tyr Glu Val Gly Thr Glu Glu Val Gly Gly Leu Gln Ala Glu
            195                 200                 205

Ala Arg Met Ala Glu Phe Leu Asp Arg Leu Trp Thr Val Leu Asp Arg
210                 215                 220

Glu Gly Leu Pro Arg Pro Val Phe Val Val Gly Asp Ile Gly Thr Arg
225                 230                 235                 240

Leu Asp Thr His Thr Phe Asp Phe Glu Arg Ala Arg Arg Leu Asp Ala
                245                 250                 255

Leu Val Arg Arg Tyr Gly Ala Leu Ile Lys Gly His Tyr Thr Asp Gly
            260                 265                 270

Val Asp Arg Leu Asp Leu Tyr Pro Gln Ala Gly Ile Gly Gly Ala Asn
            275                 280                 285

Val Gly Pro Gly Leu Ala Ala Ile Glu Phe Glu Ala Leu Glu Ala Leu
290                 295                 300

Val Ala Glu Ala His Arg Arg Lys Leu Pro Val Thr Phe Asp Arg Thr
305                 310                 315                 320

Ile Arg Gln Ala Val Ile Glu Ser Gly Arg Trp Gln Lys Trp Leu Arg
                325                 330                 335

Pro Glu Glu Lys Gly Arg Pro Phe Glu Ala Leu Pro Glu Arg Gln
            340                 345                 350

Arg Trp Leu Val Ala Thr Gly Ser Arg Tyr Val Trp Thr His Pro Ala
            355                 360                 365

Val Arg Gln Ala Arg His Gln Leu Tyr Gln Val Leu Ala Pro Trp Leu
370                 375                 380

Asp Ala Asp Ala Phe Val Arg Ala Arg Ile Lys Ala Arg Leu Met Asp
385                 390                 395                 400

Tyr Phe Arg Ala Phe Asn Leu Ile Gly Phe Asn Glu Arg Leu Gln Ala
                405                 410                 415

Phe Leu Pro Asn
            420

<210> SEQ ID NO 12
<211> LENGTH: 1263
<212> TYPE: DNA
<213> ORGANISM: Unknown
<220> FEATURE:
<223> OTHER INFORMATION: Rhodothermus profundi
<220> FEATURE:

```
<221> NAME/KEY: gene
<222> LOCATION: (1)..(1263)
<223> OTHER INFORMATION: Tagatose-biphosphate aldolase

<400> SEQUENCE: 12
atgcaggcgc acgtcctgct tgcccttcg ttcgagcagc tagcagacca caggcacgga      60
tttgttggct ggttggtcga tttgctgcgc ggaccgctgg cttaccggca cacgctgctg     120
gccgtatgtc ccaattccga agccgtaacg cgcgccgccc tggaagctgc gcgcgaagcc     180
aacgccccgc tattttttgc ggctaccctg aaccaggtcg acctggatgg cggatatacc     240
ggctggaccc cggccacgct ggctcgtttt gttgccgacg agcgcatccg cctgggcctt     300
cgcgcccctg tcgtacttgg tctggatcac ggtggcccct ggaaaaagga ttggcatgtc     360
cgcaaccgtc ttccgtacga ggcaacgctc caggcggtgc ttcgcgcgat tgaggcctgc     420
ctcgacgcag gttatgggct gcttcatctg gacccgacgg tagatctgga attgccgccc     480
ggcacacccg tccccatccc acgtattgtc gaacgaacgg tagcgctttt acaacatgct     540
gaaacgtatc gccaacagcg tcgcctgccc ccggtcgcct acgaggtagg cacggaggag     600
gttggcggcg gcctgcaggc tgaggcgcga atggcagaat ttctggatcg actctggacc     660
gtcctggatc gggaagggct accccgtccg gtgtttgtgg tgggtgacat ggcaccccgg     720
cttgacacgc acaccttcga ctttgaacgc gcccgtcgcc tggatgccct ggtgcgccgc     780
tacggtgccc tgatcaaggg gcactacacc gatggagtag accgcctgga tctatatcca     840
caggcgggta tcggtggagc aaacgtgggg cctggcctgg ctgctatcga gtttgaagcg     900
ctggaggccc tggtggccga agcgcaccgc cgcaagctgc ccgttaccct tgaccggacc     960
atccgccagg ctgtcattga agtggacgc tggcaaaaat ggctgcgccc tgaagagaaa    1020
ggacgtccct ttgaagcatt acctccagaa cgccagcggt ggctggtcgc tacaggcagc    1080
cgctacgtgt ggacgcaccc ggctgtccgg caggcgcgcc atcaattgta tcaggtgctc    1140
gctcctggc tcgatgccga tgcttttgtg cgcgcgcgca tcaaggcccg cctgatggac    1200
tacttccgcg ctttcaacct gataggcttc aatgaacggc tgcaggcctt tttacctaat    1260
tga                                                                  1263

<210> SEQ ID NO 13
<211> LENGTH: 420
<212> TYPE: PRT
<213> ORGANISM: Unknown
<220> FEATURE:
<223> OTHER INFORMATION: Rhodothermus marinus
<220> FEATURE:
<221> NAME/KEY: PEPTIDE
<222> LOCATION: (1)..(420)
<223> OTHER INFORMATION: Tagatose-biphosphate aldolase

<400> SEQUENCE: 13
```

Met Gln Ala Gln Ala Leu Leu Thr Val Pro Phe Asp Arg Val Ala Thr
1               5                   10                  15

His Ala Arg Gly Phe Val Gly Trp Val Ala Glu Leu Leu Gln Gly Pro
            20                  25                  30

Leu Ala Tyr Gln His Thr Leu Leu Ala Val Cys Pro Asn Ser Glu Ala
        35                  40                  45

Val Thr Arg Ala Ala Leu Glu Ala Ala Glu Ala Asn Ala Pro Leu
    50                  55                  60

Leu Phe Ala Ala Thr Leu Asn Gln Val Asp Leu Asp Gly Gly Tyr Thr
65                  70                  75                  80

Gly Trp Thr Pro Ala Thr Leu Ala Arg Phe Val Ala Asp Glu Leu Ala
                85                  90                  95

Arg Leu Asp Leu His Ile Pro Val Val Leu Gly Leu Asp His Gly Gly
            100                 105                 110

Pro Trp Lys Lys Asp Leu His Ala Arg Asn Arg Leu Ser Phe Glu Glu
        115                 120                 125

Thr Phe Gln Ala Val Leu Arg Ala Ile Glu Ala Cys Leu Asp Ala Gly
    130                 135                 140

Tyr Gly Leu Leu His Leu Asp Pro Thr Val Asp Leu Glu Leu Ser Pro
145                 150                 155                 160

Gly Thr Pro Val Pro Ile Pro Arg Ile Val Glu Arg Ser Val Ala Leu
                165                 170                 175

Leu Arg His Ala Glu Thr Tyr Arg Leu Arg Arg Asn Leu Pro Pro Val
            180                 185                 190

Ala Tyr Glu Val Gly Thr Glu Glu Val Gly Gly Leu Gln Ala Glu
        195                 200                 205

Ala Arg Met Ala Glu Phe Leu Asp Arg Leu Trp Thr Ala Leu Asp Arg
    210                 215                 220

Glu Gly Leu Pro His Pro Val Phe Val Val Gly Asp Ile Gly Thr Arg
225                 230                 235                 240

Leu Asp Thr Arg Thr Phe Asp Phe Glu Arg Ala Arg Arg Leu Asp Ala
                245                 250                 255

Leu Val Arg Arg Tyr Gly Ala Leu Ile Lys Gly His Tyr Thr Asp Asp
            260                 265                 270

Val Asp Arg Leu Asp Leu Tyr Pro Lys Ala Gly Ile Gly Ala Asn
        275                 280                 285

Val Gly Pro Gly Leu Ala Ala Ile Glu Phe Glu Ala Leu Glu Ala Leu
    290                 295                 300

Val Glu Glu Ala Arg Arg Gly Leu Ser Val Thr Phe Asp Gln Ala
305                 310                 315                 320

Ile Arg Arg Ala Val Val Glu Ser Gly Arg Trp Thr Lys Trp Leu Gln
                325                 330                 335

Pro Glu Glu Lys Gly Gln Pro Phe Asp Ala Leu Asp Pro Glu Arg Gln
            340                 345                 350

Arg Trp Leu Val Ala Thr Gly Ser Arg Tyr Val Trp Thr His Pro Ala
        355                 360                 365

Val Leu Gln Ala Arg Arg Glu Leu Tyr Glu Ala Leu Ala Pro Trp Leu
    370                 375                 380

Asp Ala Asp Ala Phe Val Arg Thr Arg Ile Lys Ala Arg Leu Met Asp
385                 390                 395                 400

Tyr Phe Arg Ala Phe Asn Leu Ile His Phe Asn Glu Arg Leu Gln Ala
                405                 410                 415

Phe Leu Pro Glu
        420

<210> SEQ ID NO 14
<211> LENGTH: 1263
<212> TYPE: DNA
<213> ORGANISM: Unknown
<220> FEATURE:
<223> OTHER INFORMATION: Rhodothermus marinus
<220> FEATURE:
<221> NAME/KEY: gene
<222> LOCATION: (1)..(1263)
<223> OTHER INFORMATION: Tagatose-biphosphate aldolase

<400> SEQUENCE: 14

-continued

```
atgcaggcgc aggccctgct gaccgttcca tttgatcggg tggcgaccca cgcacgcggg      60
tttgtgggct gggtggccga actgctgcag gggcccctgg cctatcagca tacgctgctg     120
gctgtctgtc ccaattcgga agcggtaaca cgggccgcgc tggaggccgc cgccgaggcc     180
aacgccccgt gcttttttgc cgccacgctg aaccaggtgg acctcgacgg cggctacacc     240
ggctggacgc cgccacgct ggcccggttc gtggcggacg aactggcccg cctggacctg      300
cacatccccg tcgtgctcgg cctggaccac ggcggcccct ggaaaaagga tctgcacgcc     360
cgcaaccgat tgtcctttga ggaaaccttc caggccgtgc tgcgggccat cgaggcctgt     420
ctggatgccg gctacggcct gctgcacctg gatccgacgg tcgatctgga gctatcgccc     480
ggcacgccgg tgcccatccc gcgcattgtc gaacgctcgg tagcgctttt gcgtcatgcc     540
gaaacctatc gacttcgacg taacctgccg ccggtcgcct acgaggtggg caccgaagaa     600
gtcggcggcg gcctgcaggc cgaagcgcgc atggcggagt ttctggatcg cctctggacc     660
gcactggacc gggaaggcct gccccatcca gtcttcgtgg tgggcgacat cggcaccccgg    720
ctcgacacgc gcacgttcga cttcgagcgg gcccgacggc tggacgcgct ggtgcgccgc     780
tacggtgccc tcatcaaagg gcactacacc gacgacgtgg atcgcctcga tctgtacccg     840
aaggcgggca tcggcggggc caacgtgggc ccgggcctgg ccgccatcga gtttgaagcg     900
ctggaggcgc tggtggagga agcccgtcgc gcggtctttt cggtgacgtt cgatcaggcc     960
atccgccggg ccgtcgtcga aagcggacgc tggacgaagt ggctccaacc ggaagagaaa    1020
ggccagccgt tcgatgcgct ggatcccgag cggcaacgct ggctggtggc caccggcagc    1080
cgctacgtgt ggacgcatcc ggccgtcctg caggcccgcc gcgaactcta cgaggcgctc    1140
gcccctggc tcgatgccga cgctttcgtg cgcacgcgca tcaaagcacg cctgatggac     1200
tactttcgtg ccttcaacct gatccatttc aacgagcggc tgcaggcctt tctccccgaa    1260
tga                                                                 1263
```

<210> SEQ ID NO 15
<211> LENGTH: 448
<212> TYPE: PRT
<213> ORGANISM: Unknown
<220> FEATURE:
<223> OTHER INFORMATION: Limnochorda pilosa
<220> FEATURE:
<221> NAME/KEY: PEPTIDE
<222> LOCATION: (1)..(448)
<223> OTHER INFORMATION: Tagatose-biphosphate aldolase

<400> SEQUENCE: 15

```
Met Gln Thr Ser Thr Ala Tyr Val Arg Gln Val Ile Trp Gly Gln Gly
1               5                   10                  15

Thr Arg Asp Pro Arg Gly Ile Tyr Ser Val Cys Thr Ala Asp Pro Leu
            20                  25                  30

Val Leu Arg Ala Ala Leu Lys Gln Ala Val Glu Asp Gly Ser Pro Ala
        35                  40                  45

Leu Ile Glu Ala Thr Ser Asn Gln Val Asn Gln Phe Gly Gly Tyr Thr
    50                  55                  60

Gly Met Glu Pro Pro Ala Phe Val Glu Phe Val Leu Gly Leu Ala Arg
65                  70                  75                  80

Glu Met Gly Leu Pro Pro Glu Arg Leu Ile Leu Gly Gly Asp His Leu
                85                  90                  95

Gly Pro Asn Pro Trp Gln Arg Leu Ala Ala Glu Glu Ala Met Arg His
            100                 105                 110
```

Ala Cys Asp Leu Val Glu Ala Phe Val Ala Cys Gly Phe Thr Lys Ile
            115                 120                 125

His Leu Asp Ala Ser Met Pro Leu Gly Glu Glu Arg Ala Gly Gly Ala
130                 135                 140

Leu Ser Lys Arg Val Val Ala Glu Arg Thr Ala Gln Leu Cys Glu Ala
145                 150                 155                 160

Ala Glu Ala Ala Phe Arg Lys Arg Ser Gln Ala Glu Gly Ala Ser Ala
                165                 170                 175

Pro Pro Leu Tyr Val Ile Gly Ser Asp Val Pro Pro Gly Gly Glu
            180                 185                 190

Thr Ser Gly Ser Gln Gly Pro Lys Val Thr Thr Pro Glu Glu Phe Glu
            195                 200                 205

Glu Thr Val Ala Leu Thr Arg Ala Thr Phe His Asp Arg Gly Leu Asp
            210                 215                 220

Asp Ala Trp Gly Arg Val Ile Ala Val Val Gln Pro Gly Val Asp
225                 230                 235                 240

Phe Gly Glu Trp Gln Val His Pro Tyr Asp Arg Ala Ala Ala Ser
                245                 250                 255

Leu Thr Arg Ala Leu Thr Gln His Pro Gly Leu Ala Phe Glu Gly His
            260                 265                 270

Ser Thr Asp Tyr Gln Thr Pro Gly Arg Leu Arg Gln Met Ala Glu Asp
            275                 280                 285

Gly Ile Ala Ile Leu Lys Val Gly Pro Ala Leu Thr Phe Ala Lys Arg
            290                 295                 300

Glu Ala Leu Phe Ala Leu Asn Ala Leu Glu Ser Glu Val Leu Gly Thr
305                 310                 315                 320

Asp Gly Arg Ala Arg Arg Ser Asn Val Glu Ala Ala Leu Glu Glu Ala
                325                 330                 335

Met Leu Ala Asp Pro Arg His Trp Ser Ala Tyr Tyr Ser Gly Asp Glu
            340                 345                 350

His Glu Leu Arg Leu Lys Arg Lys Tyr Gly Leu Ser Asp Arg Cys Arg
            355                 360                 365

Tyr Tyr Trp Pro Val Pro Ser Val Gln Glu Ala Val Gln Arg Leu Leu
            370                 375                 380

Gly Asn Leu Arg Glu Ala Gly Ile Pro Leu Pro Leu Leu Ser Gln Phe
385                 390                 395                 400

Leu Pro Arg Gln Tyr Glu Arg Val Arg Glu Gly Val Leu Arg Asn Asp
                405                 410                 415

Pro Glu Glu Leu Val Leu Asp Arg Ile Arg Asp Val Leu Arg Gly Tyr
            420                 425                 430

Ala Ala Ala Val Gly Thr Gly Ala Arg Arg Ala Glu Pro Ser Pro Ala
            435                 440                 445

<210> SEQ ID NO 16
<211> LENGTH: 1347
<212> TYPE: DNA
<213> ORGANISM: Unknown
<220> FEATURE:
<223> OTHER INFORMATION: Limnochorda pilosa
<220> FEATURE:
<221> NAME/KEY: gene
<222> LOCATION: (1)..(1347)
<223> OTHER INFORMATION: Tagatose-biphosphate aldolase

<400> SEQUENCE: 16
atgcaaacct cgacggcgta cgtgaggcag gtcatttggg gtcaagggac gagggacccc       60

-continued

```
cgcggcatct actcggtctg taccgcagac ccctcgtcc ttcgggccgc cctcaagcag    120
gcggtggagg atggctcccc cgcgctgatc gaggcgacgt ccaaccaggt gaaccagttc    180
ggcgggtata cggggatgga gcccccggcg ttcgtggagt tcgtgctggg acttgcccgc    240
gagatgggac tcccgcccga gcggctgatc ctcgggggcg atcacctcgg ccccaaccca    300
tggcagcggc tggcggccga agaggccatg cggcatgcct gcgacctcgt cgaggccttc    360
gtggcctgcg gcttcaccaa gattcacctg acgccagca tgcccctggg ggaggaacgg    420
gcaggcggtg cgctttcgaa acgggtggtg gccgaacgga ccgcccagct ctgcgaggcg    480
gccgaggcgg ccttcaggaa gcggtcccag gcggaggggg cgtcggcgcc tccgctctac    540
gtcatcggct ccgacgtgcc tccgcccggc ggcgagacct ccgggagcca ggggcccaag    600
gtgaccacgc cggaggagtt cgaggagacg gtcgcgctga cgcgggcgac ctttcacgat    660
cggggcctgg acgacgcctg ggacggggtg atcgccgtgg tggtccagcc ggggtggac    720 ttcggcgagt ggcaggttca cccctacgat cgggccgccg cggcgagcct tacccgagcc    780
ttgacgcagc atccggggct ggccttcgaa gggcactcca ccgactacca gacgccgggg    840
cggcttcgcc agatggcgga agacggcatc gccatcctga aggtgggggcc ggccctcacc    900 ttcgccaagc gggaagcgct cttcgccctg aacgccctgg agtccgaagt gctggggacg    960
gacggccgag cacggcgctc caacgtcgaa gccgccctcg aagaggcgat gctcgccgat   1020
ccccgtcact ggagcgccta ctacagcggg gacgagcacg agctccgtct caagcggaag   1080
tacgccctct ccgaccggtg tcgctactac tggccccgtcc cttcggtgca ggaggccgtc   1140
cagcgcctcc ttggcaacct gcgcgaggcg gggatcccct gcccctgct gagccagttc   1200 ctgccgcgcc agtacgagcg ggtgcgggag ggcgtcctgc gcaacgaccc ggaggagctg   1260
gtcctggacc ggattcgtga cgtgttgcgg ggatatgcgg cggccgtggg gacgggcgct   1320
aggcgggcgg agccatcacc cgcgtga                                      1347
```

```
<210> SEQ ID NO 17
<211> LENGTH: 453
<212> TYPE: PRT
<213> ORGANISM: Unknown
<220> FEATURE:
<223> OTHER INFORMATION: Caldithrix abyssi
<220> FEATURE:
<221> NAME/KEY: PEPTIDE
<222> LOCATION: (1)..(453)
<223> OTHER INFORMATION: Tagatose-biphosphate aldolase

<400> SEQUENCE: 17
```

```
Met Ser Leu His Pro Leu Asn Lys Leu Ile Glu Arg His Lys Lys Gly
1               5                   10                  15

Thr Pro Val Gly Ile Tyr Ser Val Cys Ser Ala Asn Pro Phe Val Leu
            20                  25                  30

Lys Ala Ala Met Leu Gln Ala Gln Lys Asp Gln Ser Leu Leu Leu Ile
        35                  40                  45

Glu Ala Thr Ser Asn Gln Val Asp Gln Phe Gly Gly Tyr Thr Gly Met
    50                  55                  60

Arg Pro Glu Asp Phe Lys Thr Met Thr Leu Glu Leu Ala Ala Glu Asn
65                  70                  75                  80

Asn Tyr Asp Pro Gln Gly Leu Ile Leu Gly Gly Asp His Leu Gly Pro
                85                  90                  95

Asn Arg Trp Thr Lys Leu Ser Ala Ser Arg Ala Met Asp Tyr Ala Arg
            100                 105                 110
```

Glu Gln Ile Ala Ala Tyr Val Lys Ala Gly Phe Ser Lys Ile His Leu
            115                 120                 125

Asp Ala Thr Met Pro Leu Gln Asn Asp Ala Thr Asp Ser Ala Gly Arg
        130                 135                 140

Leu Pro Val Glu Thr Ile Ala Gln Arg Thr Ala Glu Leu Cys Ala Val
145                 150                 155                 160

Ala Glu Gln Thr Tyr Arg Gln Ser Asp Gln Leu Phe Pro Pro Pro Val
                165                 170                 175

Tyr Ile Val Gly Ser Asp Val Pro Ile Pro Gly Gly Ala Gln Glu Ala
            180                 185                 190

Leu Asn Gln Ile His Ile Thr Glu Val Lys Glu Val Gln Gln Thr Ile
        195                 200                 205

Asp His Val Arg Arg Ala Phe Glu Lys Asn Gly Leu Glu Ala Ala Tyr
    210                 215                 220

Glu Arg Val Cys Ala Val Val Gln Pro Gly Val Glu Phe Ala Asp
225                 230                 235                 240

Gln Ile Val Phe Glu Tyr Ala Pro Asp Arg Ala Ala Ala Leu Lys Asp
                245                 250                 255

Phe Ile Glu Ser His Ser Gln Leu Val Tyr Glu Ala His Ser Thr Asp
            260                 265                 270

Tyr Gln Thr Ala Pro Leu Leu Arg Gln Met Val Lys Asp His Phe Ala
        275                 280                 285

Ile Leu Lys Val Gly Pro Ala Leu Thr Phe Ala Leu Arg Glu Ala Ile
    290                 295                 300

Phe Ala Leu Ala Phe Met Glu Lys Glu Leu Leu Pro Leu His Arg Ala
305                 310                 315                 320

Leu Lys Pro Ser Ala Ile Leu Glu Thr Leu Asp Gln Thr Met Asp Lys
                325                 330                 335

Asn Pro Ala Tyr Trp Gln Lys His Tyr Gly Gly Thr Lys Glu Glu Val
            340                 345                 350

Arg Phe Ala Gln Arg Phe Ser Leu Ser Asp Arg Ile Arg Tyr Tyr Trp
        355                 360                 365

Pro Phe Pro Lys Val Gln Lys Ala Leu Arg Gln Leu Leu Lys Asn Leu
    370                 375                 380

Gln Gln Ile Ser Ile Pro Leu Thr Leu Val Ser Gln Phe Met Pro Glu
385                 390                 395                 400

Glu Tyr Gln Arg Ile Arg Gln Gly Thr Leu Thr Asn Asp Pro Gln Ala
                405                 410                 415

Leu Ile Leu Asn Lys Ile Gln Ser Val Leu Lys Gln Tyr Ala Glu Ala
            420                 425                 430

Thr Gln Ile Gln Asn Ser Leu Thr Phe Thr Gln Asn Gln Asn Ser Leu
        435                 440                 445

Ala Met Glu Arg Leu
    450

<210> SEQ ID NO 18
<211> LENGTH: 1362
<212> TYPE: DNA
<213> ORGANISM: Unknown
<220> FEATURE:
<223> OTHER INFORMATION: Caldithrix abyssi
<220> FEATURE:
<221> NAME/KEY: gene
<222> LOCATION: (1)..(1362)
<223> OTHER INFORMATION: Tagatose-biphosphate aldolase

<400> SEQUENCE: 18

```
atgagtctgc atcctttaaa taaattaatc gagcgacaca aaaaaggaac gccggtcggt      60
atttattccg tctgttcggc caatcccttt gttttgaaag cggccatgct acaggcgcaa     120
aaggatcagt ctttgctact tattgaggcc acttccaacc aggtagatca attcggcggt     180
tacaccggca tgcggcccga agattttaaa acaatgacgc ttgaactggc agccgaaaac     240
aattacgatc cacagggatt aatcctgggc ggcgaccatc tggggcccaa ccgctggaca     300
aaactgagcg cctcccgggc catggactac gccagagagc agattgccgc ttatgttaaa     360
gccggctttt ccaaaatcca cttagacgcc accatgccct gcaaaacga tgccacagat      420
tccgccggcc gccttccagt cgaaacaatc gctcaacgta ccgcagaatt atgcgccgtg     480
gccgaacaaa cttaccggca gagcgaccaa ctctttccgc cgcctgttta cattgtcggc     540
agcgacgtgc ccatcccggg cggcgcgcaa gaagcgctga ccagatcca tattacggag      600
gtaaaagagg ttcaacagac cattgatcac gtgcggcggg cctttgaaaa aaacggcctg     660
gaagcggctt acgaaagagt ttgcgccgtt gtcgtgcagc caggcgttga attcgccgat     720
caaatcgttt ttgaatacgc tcccgacaga gcggcggcct aaaagatttt tattgaaagc     780
cattcgcagc tggtttatga agcgcactct actgattacc agaccgcacc tcttttgcgc     840
cagatggtaa agatcacttt gccattttta aggtcgggc ctgcgctcac ctttgccctg      900
cgcgaagcca ttttgctct ggcctttatg aaaaagagc ttttgccatt gcacagagcg       960
ctcaaacctt ctgccattct ggaaacgctg accaaacga tggacaaaaa ccctgcttac     1020
tggcaaaagc attacggcgg aacaaaggaa gaagtacgct ttgcgcagcg gtttagcctg     1080
agcgaccgca ttcgttacta ctggccgttt ccaaaggttc aaaaggccct gcgccaattg     1140
ctaaaaaact tgcaacaaat ttccattcct ctaactttgg taagccagtt catgccagag     1200
gaataccaac gtattcgcca aggaacgtta accaacgatc cgcaggcgct gattttgaac     1260
aaaattcaaa gcgtattaaa gcaatacgcg gaggcgacga aaattcaaaa ctctttgaca     1320
ttcacgcaaa atcaaaattc attagcaatg gagcgactat ga                       1362
```

<210> SEQ ID NO 19
<211> LENGTH: 429
<212> TYPE: PRT
<213> ORGANISM: Unknown
<220> FEATURE:
<223> OTHER INFORMATION: Caldicellulosiruptor kronotskyensis
<220> FEATURE:
<221> NAME/KEY: PEPTIDE
<222> LOCATION: (1)..(429)
<223> OTHER INFORMATION: Tagatose-biphosphate aldolase

<400> SEQUENCE: 19

```
Met Ser Pro Gln Asn Pro Leu Ile Gly Leu Phe Lys Asn Arg Glu Lys
1               5                   10                  15

Glu Phe Lys Gly Ile Ile Ser Val Cys Ser Ser Asn Glu Ile Val Leu
            20                  25                  30

Glu Ala Val Leu Lys Arg Met Lys Asp Thr Asn Leu Pro Ile Ile Ile
        35                  40                  45

Glu Ala Thr Ala Asn Gln Val Asn Gln Phe Gly Gly Tyr Ser Gly Leu
    50                  55                  60

Thr Pro Ser Gln Phe Lys Glu Arg Val Ile Lys Ile Ala Gln Lys Val
65                  70                  75                  80

Asp Phe Pro Leu Glu Arg Ile Ile Leu Gly Gly Asp His Leu Gly Pro
                85                  90                  95
```

Phe Val Trp Arg Asp Gln Glu Pro Glu Ile Ala Met Glu Tyr Ala Lys
                100                 105                 110

Gln Met Ile Lys Glu Tyr Ile Lys Ala Gly Phe Thr Lys Ile His Ile
            115                 120                 125

Asp Thr Ser Met Pro Leu Lys Gly Glu Asn Ser Ile Asp Asp Glu Ile
130                 135                 140

Ile Ala Lys Arg Thr Ala Val Leu Cys Arg Ile Ala Glu Glu Cys Phe
145                 150                 155                 160

Glu Lys Ile Ser Ile Asn Asn Pro Tyr Ile Thr Arg Pro Val Tyr Val
                165                 170                 175

Ile Gly Ala Asp Val Pro Pro Gly Gly Glu Ser Ser Ile Cys Gln
            180                 185                 190

Thr Ile Thr Thr Lys Asp Glu Leu Glu Arg Ser Leu Glu Tyr Phe Lys
        195                 200                 205

Glu Ala Phe Lys Lys Glu Gly Ile Glu His Val Phe Asp Tyr Val Val
210                 215                 220

Ala Val Val Ala Asn Phe Gly Val Glu Phe Gly Ser Asp Glu Ile Val
225                 230                 235                 240

Asp Phe Asp Met Glu Lys Val Lys Pro Leu Lys Glu Leu Leu Ala Lys
                245                 250                 255

Tyr Asn Ile Val Phe Glu Gly His Ser Thr Asp Tyr Gln Thr Lys Glu
            260                 265                 270

Asn Leu Lys Arg Met Val Glu Cys Gly Ile Ala Ile Leu Lys Val Gly
        275                 280                 285

Pro Ala Leu Thr Phe Thr Leu Arg Glu Ala Leu Val Ala Leu Ser His
290                 295                 300

Ile Glu Glu Glu Ile Tyr Ser Asn Glu Lys Lys Leu Ser Arg Phe
305                 310                 315                 320

Arg Glu Val Leu Leu Asn Thr Met Leu Thr Cys Lys Asp His Trp Ser
                325                 330                 335

Lys Tyr Phe Asp Glu Asn Asp Lys Leu Ile Lys Ser Lys Leu Leu Tyr
            340                 345                 350

Ser Tyr Leu Asp Arg Trp Arg Tyr Tyr Phe Glu Asn Glu Ser Val Lys
        355                 360                 365

Ser Ala Val Tyr Ser Leu Ile Gly Asn Leu Glu Asn Val Lys Ile Pro
370                 375                 380

Pro Trp Leu Val Ser Gln Tyr Phe Pro Ser Gln Tyr Gln Lys Met Arg
385                 390                 395                 400

Lys Lys Asp Leu Lys Asn Gly Ala Ala Asp Leu Ile Leu Asp Lys Ile
                405                 410                 415

Gly Glu Val Ile Asp His Tyr Val Tyr Ala Val Lys Glu
            420                 425

<210> SEQ ID NO 20
<211> LENGTH: 1290
<212> TYPE: DNA
<213> ORGANISM: Unknown
<220> FEATURE:
<223> OTHER INFORMATION: Caldicellulosiruptor kronotskyensis
<220> FEATURE:
<221> NAME/KEY: gene
<222> LOCATION: (1)..(1290)
<223> OTHER INFORMATION: Tagatose-biphosphate aldolase

<400> SEQUENCE: 20
atgagtcctc aaaatccatt gattggttta tttaagaata gagaaaaaga gtttaagggt    60

-continued

```
attatttcag tttgttcttc aaatgaaata gtcttagaag cagttttaaa aagaatgaaa      120
gatacaaacc taccaattat tattgaagcc acagcgaacc aggtaaatca atttggcggg      180
tattctgggt tgacaccgtc tcagttcaaa gaacgagtta taaaaattgc tcaaaaagtt      240
gattttccac ttgagagaat aattcttggt ggggaccatc ttggaccatt tgtgtggcgt      300
gaccaggaac cagaaattgc tatggagtat gctaagcaaa tgataaaaga atacataaaa      360
gcaggtttta ccaaaattca catcgacacg agtatgcctt taaaggggga aacagcata       420 gatgatgaaa taattgctaa agaactgct gtgctctgca ggattgcgga ggagtgtttt      480
gagaagattc tataaacaa tccctatatt acaaggccag tttatgtgat aggagctgat      540
gtgccacctc ccggcggaga gtcttctatt tgtcaaacaa ttactactaa agatgaatta      600
gaaagaagtt tagaatattt caaagaagca tttaaaaagg aaggaattga gcatgtattc      660
gattatgtag ttgctgttgt tgcaaatttt ggagttgaat ttgggagcga tgaaattgtt      720
gattttgata tggaaaaagt aaagccgcta aaagaacttt tggcaaagta caatatagta      780
tttgaaggcc attctacaga ttatcaaaca aaagaaaact taaaaagaat ggtcgaatgt      840
ggtattgcaa ttttaaaggt tggtcctgct ctaacattta cattgcgcga agcgttagta      900
gcacttagtc atattgaaga agaaatttat agcaatgaaa aggagaaact gtcaagattt      960
agagaagttt tattgaatac tatgctaaca tgcaaagatc actggagtaa atattttgat     1020
gagaatgata agttaattaa gtcaaagctc ctatatagct atcttgacag atggagatac     1080
tattttgaaa acgagagtgt gaaaagtgct gtttattctc ttattggaaa tttagagaat     1140
gttaaaattc caccttggct tgtaagtcag tattttcctt ctcagtacca aaagatgaga     1200
aaaaaagatt taaaaaacgg tgctgccgac ctaatattgg ataaaatagg ggaagtcatt     1260
gaccattatg tttatgcggt aaaagaataa                                      1290
```

<210> SEQ ID NO 21
<211> LENGTH: 408
<212> TYPE: PRT
<213> ORGANISM: Unknown
<220> FEATURE:
<223> OTHER INFORMATION: Caldilinea aerophila
<220> FEATURE:
<221> NAME/KEY: PEPTIDE
<222> LOCATION: (1)..(408)
<223> OTHER INFORMATION: Tagatose-biphosphate aldolase

<400> SEQUENCE: 21

Met Ser Thr Leu Arg His Ile Ile Leu Arg Leu Ile Glu Leu Arg Glu
1               5                   10                  15

Arg Glu Gln Ile His Leu Thr Leu Leu Ala Val Cys Pro Asn Ser Ala
            20                  25                  30

Ala Val Leu Glu Ala Ala Val Lys Val Ala Ala Arg Cys His Thr Pro
        35                  40                  45

Met Leu Phe Ala Ala Thr Leu Asn Gln Val Asp Arg Asp Gly Gly Tyr
    50                  55                  60

Thr Gly Trp Thr Pro Ala Gln Phe Val Ala Glu Met Arg Arg Tyr Ala
65                  70                  75                  80

Val Arg Tyr Gly Cys Thr Thr Pro Leu Tyr Pro Cys Leu Asp His Gly
                85                  90                  95

Gly Pro Trp Leu Lys Asp Arg His Ala Gln Glu Lys Leu Pro Leu Asp
            100                 105                 110

Gln Ala Met His Glu Val Lys Leu Ser Leu Thr Ala Cys Leu Glu Ala

```
            115                 120                 125
Gly Tyr Ala Leu Leu His Ile Asp Pro Thr Val Asp Arg Thr Leu Pro
    130                 135                 140

Pro Gly Glu Ala Pro Leu Val Pro Ile Val Val Glu Arg Thr Val Glu
145                 150                 155                 160

Leu Ile Glu His Ala Glu Gln Glu Arg Gln Arg Leu Asn Leu Pro Ala
                165                 170                 175

Val Ala Tyr Glu Val Gly Thr Glu Glu Val His Gly Gly Leu Val Asn
            180                 185                 190

Phe Asp Asn Phe Val Ala Phe Leu Asp Leu Leu Lys Ala Arg Leu Glu
        195                 200                 205

Gln Arg Ala Leu Met His Ala Trp Pro Ala Phe Val Val Ala Gln Val
    210                 215                 220

Gly Thr Asp Leu His Thr Thr Tyr Phe Asp Pro Ser Ala Ala Gln Arg
225                 230                 235                 240

Leu Thr Glu Ile Val Arg Pro Thr Gly Ala Leu Leu Lys Gly His Tyr
                245                 250                 255

Thr Asp Trp Val Glu Asn Pro Ala Asp Tyr Pro Arg Val Gly Met Gly
            260                 265                 270

Gly Ala Asn Val Gly Pro Glu Phe Thr Ala Ala Glu Phe Glu Ala Leu
        275                 280                 285

Glu Ala Leu Glu Arg Arg Glu Gln Arg Leu Cys Ala Asn Arg Lys Leu
    290                 295                 300

Gln Pro Ala Cys Phe Leu Ala Ala Leu Glu Glu Ala Val Val Ala Ser
305                 310                 315                 320

Asp Arg Trp Arg Lys Trp Leu Gln Pro Asp Glu Ile Gly Lys Pro Phe
                325                 330                 335

Ala Glu Leu Thr Pro Ala Arg Arg Trp Leu Val Gln Thr Gly Ala
            340                 345                 350

Arg Tyr Val Trp Thr Ala Pro Lys Val Ile Ala Ala Arg Glu Gln Leu
        355                 360                 365

Tyr Ala His Leu Ser Leu Val Gln Ala Asp Pro His Ala Tyr Val Val
    370                 375                 380

Glu Ser Val Ala Arg Ser Ile Glu Arg Tyr Ile Asp Ala Phe Asn Leu
385                 390                 395                 400

Tyr Asp Ala Ala Thr Leu Leu Gly
                405

<210> SEQ ID NO 22
<211> LENGTH: 1227
<212> TYPE: DNA
<213> ORGANISM: Unknown
<220> FEATURE:
<223> OTHER INFORMATION: Caldilinea aerophila
<220> FEATURE:
<221> NAME/KEY: gene
<222> LOCATION: (1)..(1227)
<223> OTHER INFORMATION: Tagatose-biphosphate aldolase

<400> SEQUENCE: 22
atgtcaacac ttcgccacat cattttgcga ctgatcgagc tgcgtgaacg agaacagatc    60
catctcacgc tgctggccgt ctgtcccaac tcggcggcgg tgctggaggc agcggtgaag   120
gtcgccgcgc gctgccacac gccgatgctc ttcgctgcca cgctcaatca gtcgatcgc   180 gacggcggct acaccggttg acgcctgcg caattcgtcg ccgagatgcg tcgctatgcc   240
gtccgctatg gctgcaccac cccgctctat ccttgcctgg atcacggcgg gccgtggctc   300
```

```
aaagatcgcc atgcacagga aaagctaccg ctcgaccagg cgatgcatga ggtcaagctg    360
agcctcaccg cctgtctgga ggccggctac gcgctgctgc acatcgaccc cacggtcgat    420
cgcacgctcc cgcccggaga agcgccgctc gtgccgatcg tcgtcgagcg cacggtcgag    480
ctgatcgaac atgccgaaca ggagcgacag cggctgaacc tgccggcggt cgcctatgaa    540
gtcggcaccg aagaagtaca tggcgggctg gtgaatttcg acaattttgt cgccttcttg    600
gatttgctca aggcaaggct tgaacaacgt gccctgatgc acgcctggcc cgccttcgtg    660
gtggcgcagg tcggcactga cctgcataca acgtattttg accccagtgc ggcgcaacgg    720
ctgactgaga tcgtgcgccc taccggtgca ctgttgaagg gcactacac cgactgggtc    780 gaaaatcccg ccgactatcc gagggtaggc atgggaggcg ccaacgttgg tccagagttt    840
acggcggccg agttcgaggc gctggaagcg ctggaacggc gggaacaacg gctgtgcgcc    900
aaccggaaat tgcagcccgc ctgttttttg gctgcactgg aagaggcagt agtcgcttca    960
gatcgttggc ggaagtggct ccagcccgat gagatcggca agcctttgc agaattaacg   1020 cccgcacgcc ggcgctggct cgtgcagacc ggggcacgct acgtctggac tgcgccgaaa   1080
gttatcgccg cacgcgaaca gctctatgcg cacctctccc ttgtgcaggc ggatccacat   1140
gcctacgtgg tagagtcagt cgcccggtca atcgagcgct atatcgatgc cttcaactta   1200
tacgacgccg ctacattgct tggatga                                      1227

<210> SEQ ID NO 23
<211> LENGTH: 446
<212> TYPE: PRT
<213> ORGANISM: Unknown
<220> FEATURE:
<223> OTHER INFORMATION: Thermoanaerobacter thermohydrosulfuricus
<220> FEATURE:
<221> NAME/KEY: PEPTIDE
<222> LOCATION: (1)..(446)
<223> OTHER INFORMATION: Tagatose-biphosphate aldolase

<400> SEQUENCE: 23

Met Asn Thr Glu His Pro Leu Lys Asn Val Val Lys Leu Gln Lys Lys
1               5                   10                  15

Gly Ile Pro Ile Gly Ile Tyr Ser Val Cys Ser Ala Asn Glu Ile Val
            20                  25                  30

Ile Gln Val Ala Met Glu Lys Ala Leu Ser Met Asp Ser Tyr Val Leu
        35                  40                  45

Ile Glu Ala Thr Ala Asn Gln Val Asn Gln Tyr Gly Gly Tyr Thr Asn
    50                  55                  60

Met Lys Pro Ile Asp Phe Arg Asp Phe Val Tyr Ser Ile Ala Lys Arg
65                  70                  75                  80

Ile Asn Phe Pro Glu Asn Arg Ile Ile Leu Gly Gly Asp His Leu Gly
                85                  90                  95

Pro Leu Pro Trp Lys Asn Gln Gln Ala Lys Lys Ala Met Glu Glu Ala
            100                 105                 110

Lys Glu Leu Val Lys Gln Phe Val Met Ala Gly Phe Thr Lys Ile His
        115                 120                 125

Val Asp Thr Ser Met Leu Leu Gly Asp Asp Asn Ile Asn Ile Lys Leu
    130                 135                 140

Asp Thr Glu Thr Ile Ala Glu Arg Gly Ala Ile Leu Val Ser Val Ala
145                 150                 155                 160

Glu Arg Ala Phe Glu Glu Leu Lys Lys Phe Asn Pro Tyr Ala Leu His
                165                 170                 175
```

Pro Val Tyr Val Ile Gly Ser Glu Val Pro Val Pro Gly Gly Ser Gln
            180                 185                 190

Lys Glu Asn Asn Glu Ile Gln Val Thr Lys Pro Thr Asp Phe Glu
        195                 200                 205

Glu Thr Val Glu Val Tyr Lys Ser Thr Phe Tyr Lys Tyr Gly Leu Gly
    210                 215                 220

Asn Ala Trp Glu Asp Val Val Ala Val Val Gln Ala Gly Val Glu
225                 230                 235                 240

Phe Gly Val Glu Asp Ile His Glu Tyr Asp His Gln Gln Ala Glu Asn
                245                 250                 255

Leu Val Ser Ala Leu Lys Lys Tyr Pro Asn Leu Val Phe Glu Ala His
            260                 265                 270

Ser Thr Asp Tyr Gln Pro Ala Lys Leu Leu Lys Glu Met Val Arg Asp
        275                 280                 285

Gly Phe Ala Ile Leu Lys Val Gly Pro Glu Leu Thr Phe Ala Leu Arg
    290                 295                 300

Glu Gly Leu Phe Ala Leu Asn Ile Ile Glu Lys Glu Leu Phe Lys Asp
305                 310                 315                 320

Asn His Asp Ile Glu Met Ser Asn Phe Ile Asp Ile Leu Asp Thr Ala
                325                 330                 335

Met Leu Asn Asn Pro Lys Tyr Trp Glu Gln Tyr Tyr Tyr Gly Asp Asp
            340                 345                 350

Asn Lys Ile Arg Ile Ala Arg Lys Tyr Ser Tyr Ser Asp Arg Cys Arg
        355                 360                 365

Tyr Tyr Leu Ile Glu Asn Glu Val Arg Ala Ser Met Ser Arg Leu Phe
    370                 375                 380

Lys Asn Leu Thr Asn Val Glu Ile Pro Leu Thr Leu Ile Ser Gln Tyr
385                 390                 395                 400

Met Pro Ile Gln Tyr Glu Lys Ile Arg Met Gly Leu Leu Lys Asn Asp
                405                 410                 415

Pro Glu Asn Leu Val Lys Asp Lys Ile Gly Asn Cys Ile Asp Lys Tyr
            420                 425                 430

Leu Tyr Ala Thr Asn Pro Thr Ser Gly Glu Phe Lys Leu Ile
        435                 440                 445

<210> SEQ ID NO 24
<211> LENGTH: 1341
<212> TYPE: DNA
<213> ORGANISM: Unknown
<220> FEATURE:
<223> OTHER INFORMATION: Thermoanaerobacter thermohydrosulfuricus
<220> FEATURE:
<221> NAME/KEY: gene
<222> LOCATION: (1)..(1341)
<223> OTHER INFORMATION: Tagatose-biphosphate aldolase

<400> SEQUENCE: 24
atgaatacag aacatccttt gaaaaacgtt gttaaactac aaaaaaaggg aattccaata      60
ggtatttatt cagtttgtag tgcaaatgaa atagttattc aagttgcaat ggagaaggca     120
ttgagtatgg atagttatgt tttaattgaa gcaacggcta atcaagtaaa tcaatatggt     180
ggctatacga atatgaaacc tattgatttt agagattttg tgtattctat agccaaaagg     240
ataaacttcc cagaaaatag aataatcctt ggcggggacc acttaggacc tttgccatgg     300
aaaaatcaac aagcgaaaaa agcaatggaa gaagcaaaag aacttgttaa caatttgtg      360 atggctggct ttacgaaaat tcatgtagat acaagtatgc ttcttggaga tgataacata     420

```
aatatcaaac tagatactga aactattgcg gagagaggag cgatacttgt atcagtagca    480
gaaagagctt ttgaggagtt aaaaaagttt aatccttatg ctcttcatcc agtttatgta    540
ataggtagtg aagttcctgt tccaggaggt tctcaaaaag aaaataataa tgaaatacaa    600
gtaacaaagc cgacggattt tgaagaaact gtggaagtgt ataaaagcac tttctataaa    660
tatggtttag gaaacgcatg ggaagatgtt gtagcagtgg ttgtgcaggc tggggtggaa    720
tttggagttg aagatattca tgaatatgat caccaacagg ctgaaaattt agtaagtgct    780
ttaaaaaagt atcctaattt agtatttgaa gcccactcta cggattatca acctgcaaaa    840
ctactaaaag aaatggtgag agatggattt gctatactta aagttggacc tgaattgact    900
tttgcattaa gggaaggatt gtttgctctg aatattatag aaaaagaatt atttaaagat    960
aatcatgata ttgagatgtc aaatttttatt gatatccttg atacagcaat gttaaataat   1020
ccgaagtatt gggaacagta ttattacggt gatgataata aaattagaat tgctagaaaa   1080
tacagctatt ctgatagatg taggtattat ctaatcgaaa atgaagttag agcatctatg   1140
tctaggttgt ttaaaaattt aacaaatgtt gagataccat taaccttgat aagtcagtat   1200
atgcctattc aatatgaaaa aattagaatg ggactattaa aaaatgatcc tgagaattta   1260
gtaaaagata aaattggaaa ttgcattgat aagtatttgt atgctactaa tccgacaagt   1320
ggagaattta aactaatata a                                              1341

<210> SEQ ID NO 25
<211> LENGTH: 33
<212> TYPE: DNA
<213> ORGANISM: Artificial Sequence
<220> FEATURE:
<223> OTHER INFORMATION: primer 1

<400> SEQUENCE: 25
gaccatcttg gcccataccc ctggaagggt cag                                33

<210> SEQ ID NO 26
<211> LENGTH: 33
<212> TYPE: DNA
<213> ORGANISM: Artificial Sequence
<220> FEATURE:
<223> OTHER INFORMATION: primer 2

<400> SEQUENCE: 26
ctgacccttc cagggtatgg gccaagatg gtc                                 33
```